(12) United States Patent
DiPerna et al.

(10) Patent No.: US 12,285,591 B2
(45) Date of Patent: Apr. 29, 2025

(54) TRAINING CARTRIDGE FOR MEDICAL PUMP SYSTEMS

(71) Applicant: Quasuras, Inc., Escondido, CA (US)

(72) Inventors: Kelsie DiPerna, San Diego, CA (US); Marc Goldman, San Diego, CA (US); Paul M. Diperna, Escondido, CA (US)

(73) Assignee: QUASURAS, INC., Escondido, CA (US)

(*) Notice: Subject to any disclaimer, the term of this patent is extended or adjusted under 35 U.S.C. 154(b) by 367 days.

(21) Appl. No.: 17/111,402

(22) Filed: Dec. 3, 2020

(65) Prior Publication Data

US 2021/0170094 A1    Jun. 10, 2021

Related U.S. Application Data

(60) Provisional application No. 62/944,999, filed on Dec. 6, 2019, provisional application No. 62/945,033, filed on Dec. 6, 2019.

(51) Int. Cl.
*A61M 5/142* (2006.01)
*A61M 5/14* (2006.01)
(Continued)

(52) U.S. Cl.
CPC ...... *A61M 5/14248* (2013.01); *A61M 5/1413* (2013.01); *A61M 5/142* (2013.01);
(Continued)

(58) Field of Classification Search
CPC .... G09B 23/28; G09B 23/285; G09B 23/286; A61M 2005/14288
See application file for complete search history.

(56) References Cited

U.S. PATENT DOCUMENTS

| 4,236,880 A | 12/1980 | Archibald |
| 4,594,058 A | 6/1986 | Fischell |

(Continued)

FOREIGN PATENT DOCUMENTS

| EP | 3165247 | 5/2017 |
| GB | 2548131 | 9/2017 |

(Continued)

OTHER PUBLICATIONS

Non-Final Office Action dated: Dec. 1, 2022 in U.S. Appl. No. 17/111,396, filed Dec. 3, 2020 and published as: US2021/0170095 on Jun. 10, 2021.

(Continued)

*Primary Examiner* — Jenna Zhang
(74) *Attorney, Agent, or Firm* — Schmeiser, Olsen & Watts LLP

(57) ABSTRACT

Rotary microfluidic medical pump and pumping method embodiments are discussed herein that may be used for controlled delivery of small and precise volumes of therapeutic or non-therapeutic fluids in a variety of environmental conditions. Certain medical pump and pumping method embodiments discussed herein may also be useful for the controlled delivery of certain therapeutic fluids that may be susceptible to degradation when exposed to high levels of pressure, flow velocity, shear stress or the like. Training cartridge device and method embodiments discussed herein may be useful for familiarizing patients with the medical pump systems they are using.

13 Claims, 24 Drawing Sheets

(51) Int. Cl.
  *A61M 5/145* (2006.01)
  *G09B 23/28* (2006.01)
  *G16H 40/67* (2018.01)
(52) U.S. Cl.
  CPC ........... *A61M 5/145* (2013.01); *G09B 23/285* (2013.01); *G16H 40/67* (2018.01); *A61M 2005/14268* (2013.01); *A61M 2005/14288* (2013.01); *A61M 2205/273* (2013.01); *A61M 2205/3327* (2013.01); *A61M 2205/3331* (2013.01); *A61M 2205/3553* (2013.01); *A61M 2205/50* (2013.01); *A61M 2205/52* (2013.01); *A61M 2205/6018* (2013.01); *A61M 2205/6027* (2013.01); *A61M 2205/6045* (2013.01); *A61M 2205/6072* (2013.01); *A61M 2205/8206* (2013.01)

(56) References Cited

U.S. PATENT DOCUMENTS

| | | | |
|---|---|---|---|
| RE32,303 E | 12/1986 | Lasker et al. | |
| 4,954,046 A | 9/1990 | Irvin et al. | |
| 5,165,873 A | 11/1992 | Meijer | |
| 5,399,168 A | 3/1995 | Wadsworth et al. | |
| 5,499,909 A | 3/1996 | Yamada et al. | |
| 5,573,515 A | 11/1996 | Wilson et al. | |
| 6,077,246 A | 6/2000 | Kullas et al. | |
| 6,186,982 B1 | 2/2001 | Gross et al. | |
| 6,406,458 B1 | 6/2002 | Tillander | |
| 6,620,138 B1 | 9/2003 | Marrgi et al. | |
| 6,669,669 B2 | 12/2003 | Flaherty et al. | |
| 6,742,992 B2 | 6/2004 | Davis | |
| 7,500,962 B2 | 3/2009 | Childers et al. | |
| 7,658,734 B2 | 2/2010 | Adair et al. | |
| 7,789,849 B2 | 9/2010 | Busby et al. | |
| 8,029,460 B2 | 10/2011 | Rush et al. | |
| 8,056,582 B2 | 11/2011 | DiPerna | |
| 8,167,581 B2 | 5/2012 | Schneeberger et al. | |
| 8,287,495 B2 | 10/2012 | Michaud et al. | |
| 8,298,184 B2 | 10/2012 | DiPerna et al. | |
| 8,408,421 B2 | 4/2013 | DiPerna | |
| 8,448,824 B2 | 5/2013 | DiPerna | |
| 8,545,440 B2 | 10/2013 | Patrick et al. | |
| 8,573,027 B2 | 11/2013 | Rosinko et al. | |
| 8,905,731 B2 | 12/2014 | Baron | |
| 8,926,561 B2 | 1/2015 | Verhoef et al. | |
| 8,939,928 B2 | 1/2015 | Savoie et al. | |
| 8,986,253 B2 | 3/2015 | DiPerna | |
| 9,211,377 B2 | 12/2015 | DiPerna et al. | |
| 9,250,106 B2 | 2/2016 | Rosinko et al. | |
| 9,295,779 B2 | 3/2016 | Kamen et al. | |
| 9,675,756 B2 | 6/2017 | Kamen et al. | |
| 9,737,656 B2 | 8/2017 | Rosinko | |
| 10,010,674 B2 | 7/2018 | Rosinko et al. | |
| 10,213,546 B2 | 2/2019 | Anderson et al. | |
| 10,279,106 B1 | 5/2019 | Cook et al. | |
| 11,464,899 B2 | 10/2022 | Searle et al. | |
| 2002/0004643 A1 | 1/2002 | Carmel et al. | |
| 2004/0034331 A1 | 2/2004 | Toman et al. | |
| 2004/0257413 A1 | 12/2004 | Anderson et al. | |
| 2005/0038386 A1 | 2/2005 | Fago et al. | |
| 2005/0119611 A1 | 6/2005 | Marano-Ford et al. | |
| 2005/0214129 A1 | 9/2005 | Greene et al. | |
| 2008/0051716 A1 | 2/2008 | Stutz | |
| 2008/0092969 A1 | 4/2008 | DiPerna | |
| 2009/0030366 A1 | 1/2009 | Hochman | |
| 2010/0145303 A1 | 6/2010 | Yodfat et al. | |
| 2010/0185322 A1 | 7/2010 | Bylsma et al. | |
| 2010/0198182 A1 | 8/2010 | Lanigan et al. | |
| 2010/0232992 A1 | 9/2010 | Gray | |
| 2011/0021993 A1 | 1/2011 | Bar-Haim et al. | |
| 2011/0098638 A1 | 4/2011 | Chawla et al. | |
| 2011/0118694 A1* | 5/2011 | Yodfat | A61M 5/172 604/93.01 |
| 2011/0186177 A1 | 8/2011 | Lanier, Jr. et al. | |
| 2011/0196304 A1 | 8/2011 | Kramer et al. | |
| 2012/0238999 A1* | 9/2012 | Estes | A61M 5/1723 604/67 |
| 2013/0055889 A1 | 3/2013 | Herz et al. | |
| 2013/0101910 A1 | 4/2013 | Barton | |
| 2013/0150824 A1 | 6/2013 | Estes et al. | |
| 2013/0236872 A1* | 9/2013 | Laurusonis | G09B 23/285 434/262 |
| 2013/0237947 A1 | 9/2013 | Amirouche et al. | |
| 2014/0134561 A1 | 5/2014 | Smith et al. | |
| 2014/0228762 A1 | 8/2014 | Capone et al. | |
| 2014/0276422 A1 | 9/2014 | Reilly et al. | |
| 2014/0378903 A1 | 12/2014 | Quinlan | |
| 2014/0378943 A1 | 12/2014 | Geipel | |
| 2015/0085179 A1 | 3/2015 | Van Heugten | |
| 2015/0106113 A1 | 4/2015 | Reddy | |
| 2015/0273201 A1 | 10/2015 | Tallarida et al. | |
| 2015/0290445 A1 | 10/2015 | Powers et al. | |
| 2015/0343143 A1 | 12/2015 | Estes et al. | |
| 2015/0352296 A1 | 12/2015 | Yodfat et al. | |
| 2015/0366945 A1 | 12/2015 | Greene | |
| 2016/0038675 A1* | 2/2016 | Estes | G16H 40/67 604/151 |
| 2016/0120751 A1* | 5/2016 | Mounce | A61P 19/10 604/404 |
| 2016/0129178 A1 | 5/2016 | Askarinya et al. | |
| 2016/0151560 A1 | 6/2016 | Toro et al. | |
| 2016/0361489 A1 | 12/2016 | Di Perna | |
| 2017/0128709 A1 | 5/2017 | Chen | |
| 2017/0203030 A1 | 7/2017 | Brewer et al. | |
| 2017/0216520 A1 | 8/2017 | Kamen et al. | |
| 2017/0246380 A1 | 8/2017 | Rosinko et al. | |
| 2017/0286638 A1* | 10/2017 | Searle | G16H 40/63 |
| 2018/0001000 A1 | 1/2018 | Herwig et al. | |
| 2018/0085521 A1 | 3/2018 | Allis et al. | |
| 2018/0369481 A1* | 12/2018 | Pedersen | A61M 5/31511 |
| 2019/0009023 A1 | 1/2019 | Di Perna et al. | |
| 2019/0143044 A1* | 5/2019 | Paramanandam | A61M 5/20 604/187 |
| 2019/0355481 A1 | 11/2019 | Lamb et al. | |
| 2020/0030529 A1 | 1/2020 | Di Perna et al. | |
| 2020/0214625 A1 | 6/2020 | Hooven et al. | |
| 2021/0042730 A1 | 2/2021 | Lee | |
| 2021/0084700 A1 | 3/2021 | Daniels | |
| 2021/0134184 A1* | 5/2021 | Baker | G09B 23/285 |
| 2021/0170095 A1 | 6/2021 | DiPerna et al. | |
| 2022/0092960 A1 | 3/2022 | Arumugam et al. | |
| 2022/0101992 A1 | 3/2022 | Porter et al. | |
| 2023/0108800 A1 | 4/2023 | Neese et al. | |

FOREIGN PATENT DOCUMENTS

| | | | |
|---|---|---|---|
| WO | WO 15/134526 | 9/2015 | |
| WO | WO 17/194074 | 11/2017 | |
| WO | WO 19/010324 | 1/2019 | |
| WO | WO 19/079474 | 4/2019 | |
| WO | WO-2019079474 A1 * | 4/2019 | ........... G09B 19/003 |
| WO | WO 22/076337 | 4/2022 | |

OTHER PUBLICATIONS

Non-Final Office Action dated: Nov. 3, 2022 in U.S. Appl. No. 17/166,833, filed Feb. 3, 2021 and published as: US2021/0249113 on Aug. 12, 2022.
Supplementary European Search Report dated: Mar. 12, 2021 in European Patent Application No. EP 18828123.2 filed: Jul. 5, 2018.
Invitation to Pay Additional Fees dated: Feb. 23, 2021 in International Application No. PCT/US2020/63152 filed: Dec. 3, 2020.
International Preliminary Report on Patentability dated: Jan. 26, 2021 in International Application No. PCT/US2019/43146 filed: Jul. 24, 2019.
International Search Report and Written Opinion dated: Oct. 18, 2018 in International Application No. PCT/US2018/40944, filed: Jul. 5, 2018 and published as: WO/2019/010324 on Jan. 10, 2019.

(56) References Cited

OTHER PUBLICATIONS

International Search Report and Written Opinion dated: Jul. 31, 2015 in International Application No. PCT/US2015/18525 filed: Mar. 3, 2015 and published as: WO/2015/134526 on: Sep. 11, 2015.
International Search Report and Written Opinion dated: Oct. 4, 2019 in International Application No. PCT/US2019/43146 filed: Jul. 24, 2019.
Office Action dated: Jan. 2, 2020 in U.S. Appl. No. 15/122,132, filed Aug. 26, 2016 and published as: 2016/0361489 on Dec. 15, 2016.
Final Office Action dated: Jun. 26, 2020 in U.S. Appl. No. 15/122,132, filed Aug. 26, 2016 and published as: 2016/0361489 on Dec. 15, 2016.
Office Action dated: Nov. 16, 2020 in U.S. Appl. No. 16/028,256, filed Jul. 5, 2018 and published as: 2019/0009023 on Jan. 1, 2019.
International Search Report and Written Opinion dated Apr. 28, 2021 in International Patent Application No. PCT/US2020/63152 filed: Dec. 3, 2020.
International Preliminary Report on Patentability dated May 17, 2022 in International Patent Application No. PCT/US2020/63152 filed: Dec. 3, 2020.
International Search Report and Written Opinion dated Feb. 26, 2021 in International Patent Application No. PCT/US2020/63151 filed: Dec. 3, 2020.
International Preliminary Report on Patentability dated May 17, 2022 in International Patent Application No. PCT/US2020/63151 filed: Dec. 3, 2020.
Final Office Action dated: Aug. 18, 2023 in U.S. Appl. No. 17/111,396, filed Dec. 3, 2020 and published as: US2021/0170095 on Jun. 10, 2021.
Final Office Action dated: Jan. 23, 2024 in U.S. Appl. No. 17/111,396, filed Dec. 3, 2020 and published as: US2021/0170095 on Jun. 10, 2021.
Extended European Search Report dated Nov. 21, 2023 in European Patent Application No: 20896925.3 filed: Dec. 3, 2020.
Supplemental European Search Report dated: Jan. 24, 2024 in European Patent Application No. 20896021.1 filed: Dec. 3, 2020.
Final Office Action dated: Apr. 14, 2023 in U.S. Appl. No. 17/111,396, filed Dec. 3, 2020 and published as: US2021/0170095 on Jun. 10, 2021.
Final Office Action dated: Mar. 21, 2023 in U.S. Appl. No. 17/166,833, filed Feb. 3, 2021 and published as: US2021/0249113 on Aug. 12, 2022.
International Search Report and Written Opinion dated Feb. 23, 2023 in International Patent Application No. PCT/US2022/045065 filed: Sep. 28, 2022 and published as: WO/2023/055819 on: Apr. 6, 2023.
Non-Final Office Action dated: Jun. 6, 2024 in U.S. Appl. No. 17/111,396, filed Dec. 3, 2020 and published as: US2021/0170095 on Jun. 10, 2021.
Non-Final Office Action dated: Jul. 3, 2024 in U.S. Appl. No. 18/485,156, filed Oct. 11, 2023 and published as: US2024/0038359 on Feb. 1, 2024.
Notice of Allowance dated: Nov. 27, 2024 in U.S. Appl. No. 18/485,156, filed Oct. 11, 2023 and published as: US2024/0038359 on Feb. 1, 2024.
Final Office Action dated: Oct. 24, 2024 in U.S. Appl. No. 17/111,396, filed Dec. 3, 2020 and published as: US 2021-0170095 A1 on: Jun. 10, 2021.

* cited by examiner

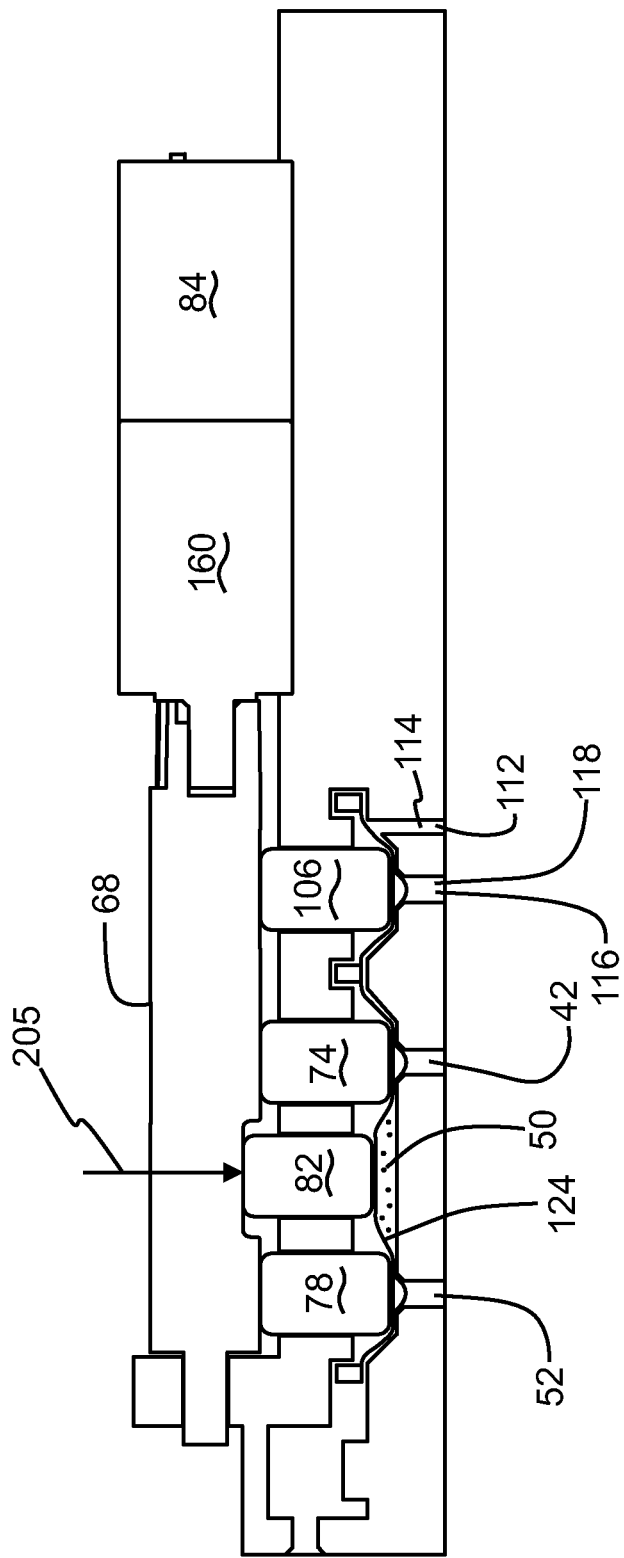

TRAINING CARTRIDGE FOR MEDICAL PUMP SYSTEMS

RELATED APPLICATIONS

This application claims priority under 35 U.S.C. section 119(e) from U.S. Provisional Patent Application No. 62/945,033, filed Dec. 6, 2019, by P. DiPerna et al., and titled "Rotary Microfluidic Pump", and from U.S. Provisional Patent Application No. 62/944,999, filed Dec. 6, 2019, by K. DiPerna et al., and titled "Medical Device Training Module", each of which is hereby incorporated by reference in its entirety.

BACKGROUND

The delivery of therapeutic and non-therapeutic medical fluids is commonly performed intravenously (IV) or subcutaneously using an infusion catheter or cannula and a syringe pump. The mechanism of such syringe type pumps typically compresses a syringe plunger within a corresponding syringe housing in a controlled fashion to provide accurate dosing. For ambulatory pumps this mechanism may be scaled down but generally the small, powerful, and accurate motor that is required for such syringe pumps is expensive. Syringe pumps typically also rely on a motor driven lead screw and attachment to a compressing plunger to not only control the delivery of fluids but also to prevent the unexpected delivery of fluids to a patient over a prolonged period of use by the patient. The accuracy of syringe type pumps as well as other common medical pumps, including peristaltic type pumps, may be compromised by changes in environmental conditions including variation in ambient temperature, changes in ambient pressure as well as other factors. What have been needed are improved pumping mechanisms and methods that are reasonably priced and that can reliably deliver small quantities of medical fluids in an accurate and consistent manner without susceptibility to environmental variations. What have also been needed are devices and methods for assisting patient end users of medical pumps become familiar and confident with the operation of the medical pump systems they are using.

SUMMARY

Some embodiments of a medical pump system may include a reservoir cartridge assembly having a fluid reservoir. The fluid reservoir may include a liquid volume, an air volume and a flexible membrane disposed between the liquid volume and air volume which is configured to provide a fluid tight barrier between the liquid volume and air volume. The reservoir cartridge assembly may also include a pump chamber assembly that has a pump chamber with an interior volume which is at least partially bounded by a pump housing. The pump chamber may further include an inlet port in fluid communication with the interior volume and with the liquid volume of the fluid reservoir, and a resilient inlet membrane which is disposed adjacent the inlet port, which is spaced from the inlet port when in a relaxed state, and which is sufficiently distendable towards the inlet port to seal the inlet port in a compressed state. The pump chamber may also include an outlet port in fluid communication with the interior volume and with an outlet conduit. The pump chamber assembly may also include and a resilient outlet membrane which is disposed adjacent the outlet port, which is spaced from the outlet port when in a relaxed state, and which is sufficiently distendable towards the outlet port to seal the outlet port in a compressed state. The pump chamber may also have a displacement chamber disposed within the interior volume and a resilient displacement membrane. The resilient displacement membrane may be disposed adjacent the displacement chamber, form at least a portion of a boundary of the displacement chamber, be sufficiently inwardly distendable from a relaxed state to reduce the volume of the displacement chamber when in a compressed state, and be sufficiently resilient to rebound and increase the volume of the displacement chamber when released from the compressed state. The medical pump system may also include an actuator assembly that is configured to be operatively and releasably coupled to the reservoir cartridge assembly. The actuator assembly may include a cam assembly including an inlet cam lobe which is operatively coupled to the resilient inlet membrane, an outlet cam lobe which is operatively coupled to the resilient outlet membrane, and a displacement cam lobe which is operatively coupled to the displacement membrane. The actuator assembly may also have a motor operatively coupled to the cam assembly and a controller operatively coupled to the motor.

Some embodiments of a reservoir cartridge assembly which is configured to be operatively and releasably coupled to an actuator assembly of a medical pump system may include a reservoir base and a fluid reservoir disposed on the reservoir base. The fluid reservoir may include a liquid volume, an air volume and a flexible membrane disposed between the liquid volume and air volume. The flexible membrane may be configured to provide a fluid tight barrier between the air volume and the liquid volume. The reservoir cartridge assembly may further include a pump chamber assembly secured to the reservoir base. The pump chamber assembly may have a pump chamber with an interior volume which is at least partially bounded by a pump housing. The pump chamber assembly may also have an inlet port in fluid communication with the interior volume and in fluid communication with the liquid volume of the fluid reservoir. The pump chamber assembly may further include a resilient inlet membrane which is disposed adjacent the inlet port, which is spaced from the inlet port when in a relaxed state, and which is sufficiently distendable towards the inlet port to seal the inlet port in a compressed state. An outlet port in fluid communication with the interior volume and with an outlet conduit is also included with the pump chamber assembly, as well as a resilient outlet membrane which is disposed adjacent the outlet port, which is spaced from the outlet port when in a relaxed state, and which is sufficiently distendable towards the outlet port to seal the outlet port in a compressed state. The pump chamber assembly also has a displacement chamber disposed within the interior volume and a resilient displacement membrane which is disposed adjacent the displacement chamber, which forms at least a portion of a boundary of the displacement chamber, which is sufficiently inwardly distendable from a relaxed state to reduce the volume of the displacement chamber when in a compressed state. The resilient displacement membrane is also sufficiently resilient to increase the volume of the displacement chamber when released from the compressed state.

Some embodiments of an actuator assembly which is configured to be operatively and releasably coupled to a reservoir cartridge assembly of a medical pump system may include an actuator chassis and a controller secured to the actuator chassis. The actuator assembly may further include a cam assembly which is disposed on the actuator chassis and which includes an inlet cam lobe which is configured to be operatively coupled to a resilient inlet membrane, an outlet cam lobe which is configured to be operatively coupled to a resilient outlet membrane, a displacement cam lobe which is configured to be operatively coupled to a displacement membrane, and a vent cam lobe which is configured to be operatively coupled to a vent membrane. The actuator assembly may also include a motor which is operatively coupled to the cam assembly and a controller. The actuator assembly may also include a pressure sensor which is operatively coupled to the controller.

Some embodiments of a pump assembly for medical use may include a pump chamber assembly having a pump chamber with an interior volume which is at least partially bounded by a pump housing. The pump chamber assembly may also have an inlet port in fluid communication with the interior volume and a resilient inlet membrane which is disposed adjacent the inlet port, which is spaced from the inlet port when in a relaxed state, and which is sufficiently distendable towards the inlet port to seal the inlet port in a compressed state. The pump chamber assembly may also include an outlet port in fluid communication with the interior volume and a resilient outlet membrane which is disposed adjacent the outlet port, which is spaced from the outlet port when in a relaxed state, and which is sufficiently distendable towards the outlet port to seal the outlet port in a compressed state. A displacement chamber may further be disposed within the interior volume. A resilient displacement membrane may be disposed adjacent the displacement chamber, form at least a portion of a boundary of the displacement chamber, be sufficiently inwardly distendable from a relaxed state to reduce the volume of the displacement chamber when in a compressed state, and be sufficiently resilient to increase the volume of the displacement chamber when released from the compressed state. The pump assembly may also include an actuator assembly which has a cam assembly with a cam shaft having an inlet cam lobe which is operatively coupled to the resilient inlet membrane, an outlet cam lobe which is operatively coupled to the resilient outlet membrane, and a displacement cam lobe which is operatively coupled to the displacement membrane. The actuator assembly may also have a motor operatively coupled to the cam assembly.

Some embodiments of a method of pumping a medical fluid may include coupling a reservoir cartridge assembly to an actuator assembly to form a medical pump system and filling a liquid volume of a fluid reservoir of the reservoir cartridge assembly with a therapeutic fluid as well as venting air from an air volume disposed adjacent the liquid volume. The method may also include disposing an outlet conduit of the pump chamber assembly in fluid communication with a subcutaneous delivery site within the patient's body and delivering a controlled rate of infusion of the therapeutic fluid to the subcutaneous delivery site of the patient by performing sequential pumping cycles of the medical pump system carried out according to a predetermined delivery protocol.

Some embodiments of a medical pump training system may include an actuator assembly having an actuator chassis and a controller secured to the actuator chassis. The medical pump training system may also include a training cartridge having a cartridge housing which is configured to releasably couple to the actuator assembly and which includes an identifying feature that is configured to be operatively coupled to the controller of the actuator assembly and provide information to the controller identifying the training cartridge as a non-therapeutic cartridge.

Some embodiments of a training cartridge for a medical pump system may include a cartridge housing that is configured to couple to an actuator assembly of the medical pump system. The training cartridge may also include an identifying feature disposed on the cartridge housing that is configured to be operatively coupled to a controller of the actuator assembly and provide information to the controller identifying the training cartridge.

Some embodiments of a multi-function medical pump may include an actuator assembly, having a latch mechanism constructed and arranged to removably couple to a cartridge and a selection mechanism that determines a type of cartridge. The multi-function medical pump may also include the cartridge, wherein a first type of cartridge is a reservoir cartridge assembly that is permitted by the latch mechanism to couple to the actuator assembly for a single use operation, and wherein a second type of cartridge is a training cartridge that is permitted by the latch mechanism to couple to the actuator assembly for multiple training operations.

Some embodiments of a method for operating a multi-function medical pump may include removably coupling an actuator assembly to a cartridge and determining by a selection mechanism a type of cartridge which has been assembled. The method may also include coupling by a latch mechanism of the multi-function medical pump the actuator assembly and the reservoir cartridge assembly for a single use operation in response to determining that the type of cartridge is a reservoir cartridge assembly. The method may also include coupling by the latch mechanism the actuator assembly and the training cartridge for multiple training use operations in response to determining that the type of cartridge is a training cartridge.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

FIGS. 14A-14C are schematic section views of the pump assembly of FIG. 13 illustrating a pumping sequence.

Figure 1:
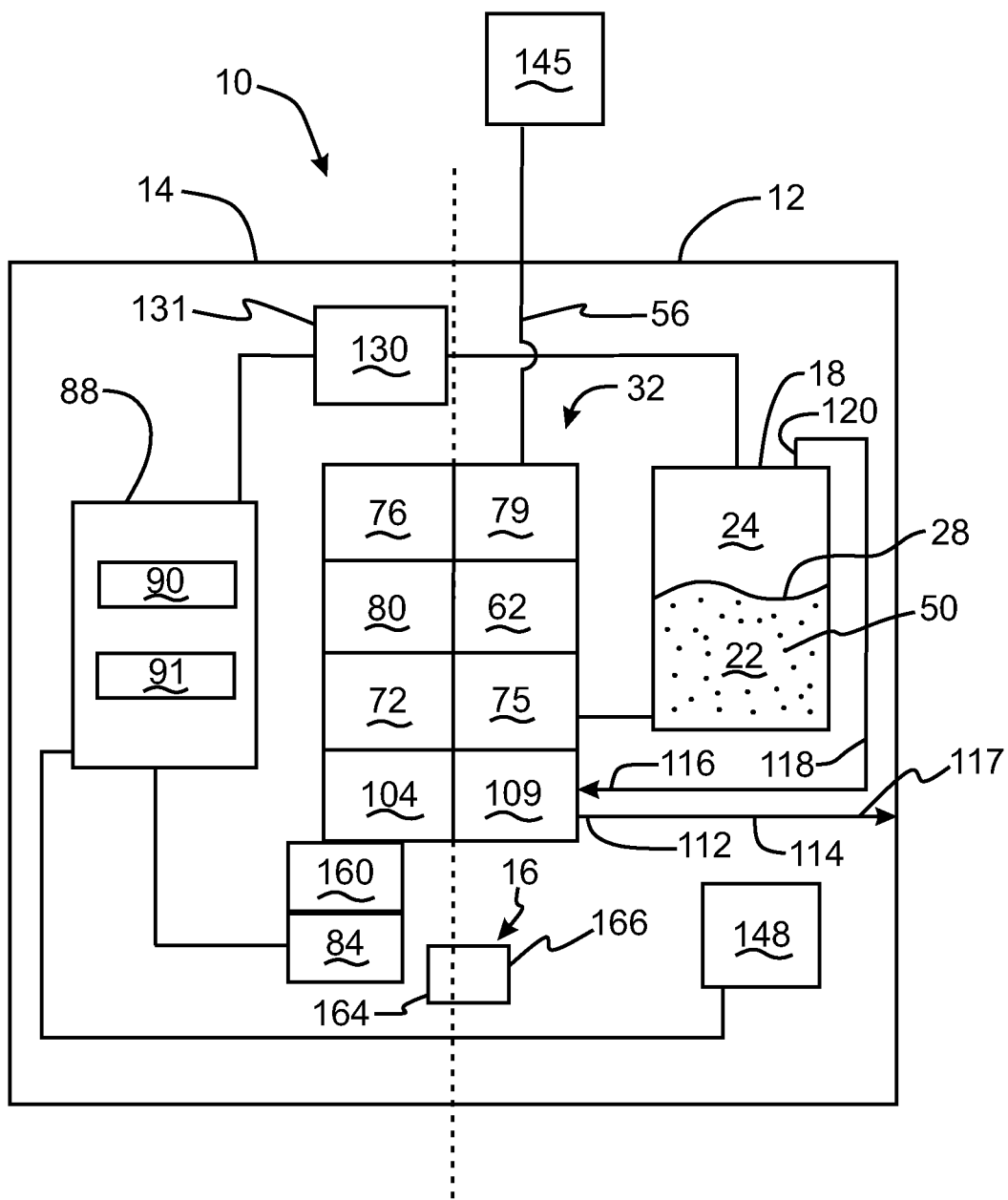
FIG. 1 is a schematic depiction of a medical pump system embodiment.

The drawings are intended to illustrate certain exemplary embodiments and are not limiting. For clarity and ease of illustration, the drawings may not be made to scale, and in some instances, various aspects may be shown exaggerated or enlarged to facilitate an understanding of particular embodiments.

DETAILED DESCRIPTION

As discussed above, delivery of therapeutic fluids or non-therapeutic medical fluids is commonly performed intravenously (IV) or subcutaneously using systems that include pumps such as syringe pumps, peristaltic pumps as well as others. However, these types of pumps do not always perform consistently and cost effectively, particularly when used in varying environmental conditions. Medical pump embodiments and related components that address issues such as these are discussed in U.S. patent application Ser. No. 16/028,256, filed Jul. 5, 2018, by P. DiPerna et al., titled "Medical Pump with Flow Control", U.S. patent application Ser. No. 16/520,521, filed Jul. 24, 2019, by P. DiPerna et al., titled "Subcutaneous Access Hub with Multiple Cannula Ports", and U.S. patent application Ser. No. 15/122,132, Publication No. US 2016/0361489 A1, filed Mar. 3, 2015, by P. DiPerna, titled "Fluid Delivery Pump", each of which is incorporated by reference herein in its entirety.

In addition, some or all of these issues may be addressed by improved medical pumping mechanisms that may include a positive displacement pump mechanism. Discussed below are embodiments of micro-positive displacement pump embodiments actuated by a cam assembly that may, in some cases, include a single camshaft synching an input valve and an output valve of a pump chamber. For some embodiments, such valve embodiments may include the use of one or more diaphragms, also referred to herein as resilient membranes, that are displaced by rotating lobes of the cam assembly. For some embodiments, the lobes of the cam assembly may be rotated by a DC motor coupled through a planetary gearset. Such positive displacement pump embodiments may be incorporated into a medical pump system that includes a reservoir cartridge assembly and a cooperating actuator assembly that may be configured to provide both convenient and economical use for an end user patent of the system.

It should be noted that in many cases, the pump embodiments discussed herein may be operated directly by medical professionals that are treating patients. In many cases, the pump embodiments discussed herein may also be operated directly by individual end users that suffer from a particular medical condition, such as diabetes or any other condition that may require accurate and reliable infusion of a therapeutic fluid. Such individual end users may be using such pump system embodiments to administer therapeutic fluids to themselves under the direction of a medical professional or any other suitable direction. In either case, the person receiving such a treatment will generally be referred to herein as a patient, although the terms end user, patient and the like may be used interchangeably.

For such embodiments, a full revolution of the cam shaft may provide a single fill and dispense cycle for a small volume of fluid from the pump chamber of the medical pump system in some cases. The inlet port and outlet port may be closed by the respective camshaft lobes by a method wherein upon rotation at a particular phase the respective cam lobe pushes down on an appropriate piston element, which may also be referred to herein as a pushrod, to compress the resilient membrane and complete a sealed closure of the port. Timing of the inlet cam lobe and outlet cam lobe may be configured by design such that either the inlet port, outlet port, or both inlet port and outlet port may be closed off at certain phases of the cam lobe rotation. The cam assembly may be configured to sequence the displacement and direction of the pushrods in order to ensure that there is never an open fluid path from a fluid reservoir of a reservoir cartridge assembly to the body of the patient, e.g., via an outlet conduit of the medical pump system to a hub of a patient port that is in fluid communication with a subcutaneous portion of a patient's body that may include a Luer™ connection to an infusion set or the like. For some such embodiments, there may be four unique states of the pushrods, e.g.: a fill state, a pre-dispense state, a dispense state, and a pre-fill state.

For some embodiments, the motor may be driven through the discharge of a capacitor which can also be useful to reduce the risk of a continuous runaway condition for the motor. The motor rotation speed may be controlled by pulsing a discharge of such a capacitor. The frequency of discharged pulses may be controlled by embedded firmware which may be configured to support partial pumping cycles, partial dispense cycles or the like. An electrical switch such as a micro-switch may be positioned onto a shaft of the cam assembly to confirm a proper or otherwise desired rotation state of the cam shaft and/or motor shaft with respect to output steps of the motor.

In some cases, a pressure sensor disposed in the actuator assembly may be configured to interface with the reservoir cartridge assembly and used to determine a pressure within an air volume of the fluid reservoir of the reservoir cartridge assembly. In some cases, the pressure sensor may be used to measure a pressure differential within the air volume when fluid is drawn from the liquid volume of the fluid reservoir to fill the pump chamber thereby reducing a volume of liquid disposed in the liquid volume. Such pressure readings may also be used to provide increased sensitivity for detecting occlusions in a fluid path of the outlet port, or outlet conduit, such as the infusion tubing, between the outlet port and hub of the infusion set.

Such a medical pump system or components thereof may be useful for delivery of non-therapeutic fluids or therapeutic fluids such as saline, antibiotics, dextrose solutions, pain medications, peptides and the like. Some therapeutic fluids that may be delivered by the medical pump system embodiments discussed herein may include therapeutic fluids used for the treatment of diabetes as well as other related medical conditions. In particular, such medical pump systems or components thereof may be useful for the continuous subcutaneous delivery of insulin, including standard insulin compositions such as Novolog®, Lyumjev™, Fiasp®, and Humalog®, fast-acting insulins such as Lispro, Aspart, and Glulisine, and slow-acting insulin compositions such as insulin Glargine and insulin Detemin. Other therapeutic fluids used for the treatment of diabetes or any other suitable medical condition where accurate and cost effective delivery of fluids to a patient is needed such as liquid stable glucagon may also be delivered. Such medical pump systems may be particularly useful where such fluid delivery is being carried out in varying environmental conditions and/or where ambulatory delivery is desirable.

For some medical pump system embodiments, cost effectiveness and efficiency may be realized by identifying a first set of components that may be included with a durable element and a second set of components that may be included with a low use or disposable single use type element of a medical pump system. For such embodiments, the more costly and/or more durable components may be included with the first set of components of the durable element in order to reuse and make efficient use of these types of components. Less expensive components, components that require frequent refreshing and/or those components that require sterilization before each use may be incorporated into the second set of components of the disposable element. As such, for some medical pump system embodiments discussed herein, the motor, transmission, cam assembly, sensitive pressure sensor, and controller which may include a microprocessor and memory may be included in a reusable actuator assembly that may be categorized as the durable element. Components such as a fluid reservoir, pump chamber and its associated elements and a power source such as a battery may be included in the reservoir cartridge assembly which may be categorized as the less durable or disposable element. Additional sub-assemblies may include a mount bracket that is configured to detachably mount the medical pump assembly to the patient's body with a single use adhesive pad that is generally serviceable for about 1 day to about 3 days, a service life that may be similar to the service life of embodiments of the reservoir cartridge assembly. In some cases, the durable element of the actuator may have a service life of up to about 6 months or more.

Pump assembly embodiments discussed herein may be configured to reduce or eliminate the possible detrimental effects of harsh and/or sudden mechanical movements upon the molecules of certain therapeutic fluids such as insulin. As such, the device and method embodiments for fluid delivery discussed herein are consistent with the cam lobes of the cam assembly embodiments rotating slowly (in some cases up to only about two revolutions per minute during bolus delivery) allowing the cam lobes to gently open and close respective ports controlled thereby so as to move the molecules of the therapeutic fluid through the pump assembly embodiments without damage to the molecules of the therapeutic fluids, such as for example insulin molecules.

Referring generally to FIGS. 1-10, a medical pump system embodiment 10 is shown that includes two major components including a reservoir cartridge assembly 12 and an actuator assembly 14 that are configured to be coupled together with a latch mechanism 16 that holds them securely together, but that can later be released to install a new reservoir cartridge assembly 12 into the reusable actuator assembly 14. A schematic overview of an embodiment of the medical pump system 10 is shown in FIG. 1 wherein a dashed line indicates a coupling interface between the actuator assembly 14 and the reservoir cartridge assembly 12, and the various components thereof. The interconnecting lines between the various schematic components of FIG. 1 may include any type of suitable conduit that may be useful for operatively interconnecting the respective components such as information conducting conduits, power conducting conduits or the like including conductive wires, optical fibers, wireless connectivity etc. In general, for some embodiments, the actuator assembly embodiment 14 may be a durable element that may be used over several months or more and the reservoir cartridge assembly 12 may be a disposable single use element that is replaced on a more frequent basis, such as every few days. The medical pump system embodiments 10 discussed herein are suitable for ambulatory use and may have outer dimensions suitable for such use. In some cases, embodiments of the medical pump systems 10 discussed herein may have a length of about 2.0 inches to about 3.0 inches, a width of about 1.2 inches to about 1.8 inches and a thickness of about 0.4 inches to about 0.7 inches.

Figure 4:
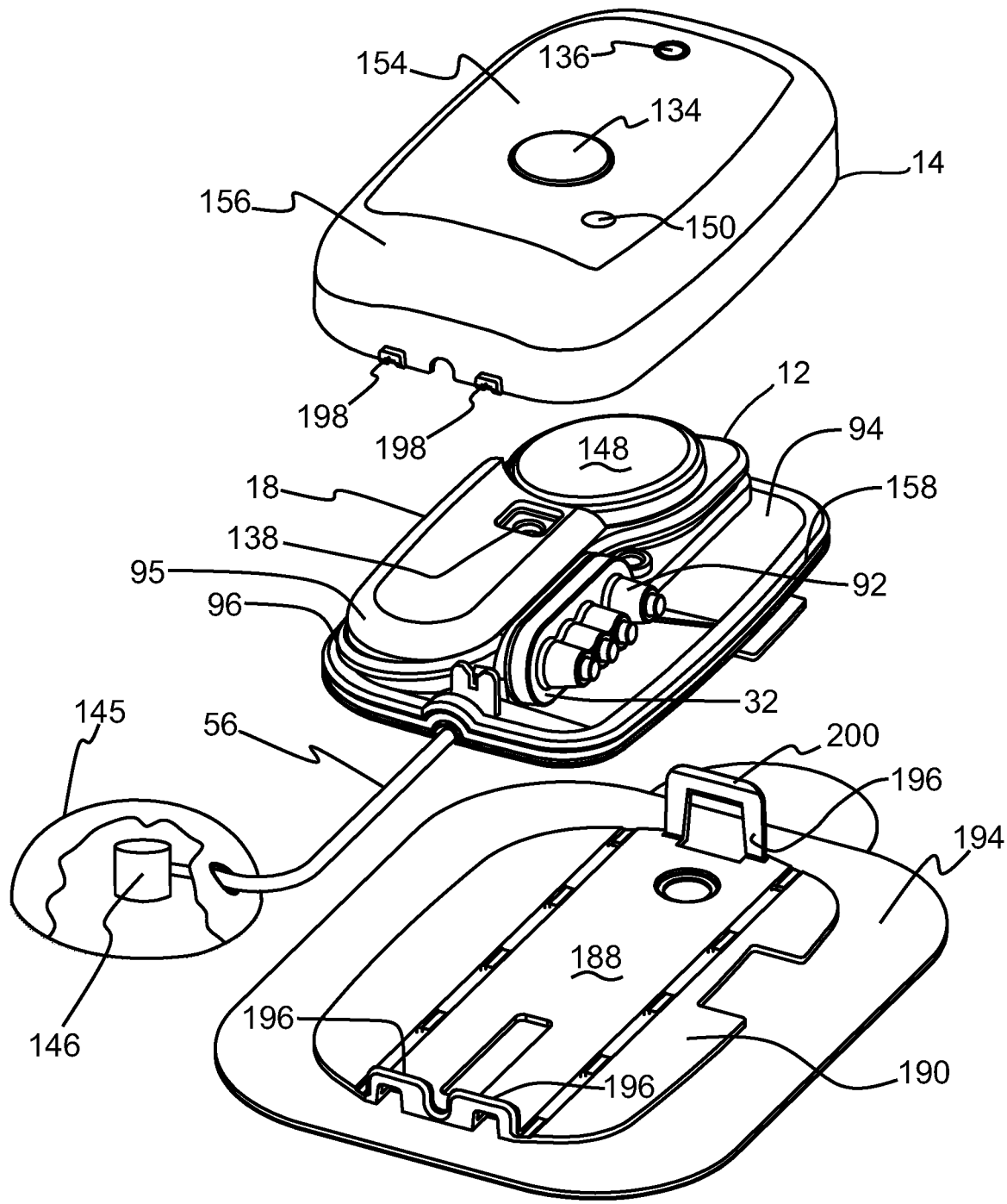
FIG. 4 is an exploded view of the medical pump system embodiment of FIG. 2.

In some cases, the reservoir cartridge assembly 12 may include a fluid reservoir 18 as shown in FIGS. 1 and 4 which may have an outer structure or container that is rigid and resistant to flexing in response to pressure differentials imposed between an inner volume thereof and the area disposed outside of the outer structure or container. In some cases, the fluid reservoir 18 may also have a liquid volume 22, an air volume 24 and a flexible membrane 28 disposed between the liquid volume 22 and air volume 24. The flexible membrane 28 may be made from a fluid tight material and thus provides a fluid tight barrier between the air volume 24 and liquid volume 22. For some embodiments, the flexible membrane 28 may be molded by methods such as cold molding in order to conform to the inner contour shape of the fluid reservoir cavity of the reservoir base 94. The outer perimeter of the flexible membrane may be sealingly secured to the outer perimeter of the fluid reservoir cavity of the reservoir base 94 by methods such as heat sealing, adhesive bonding or the like.

Figure 14:
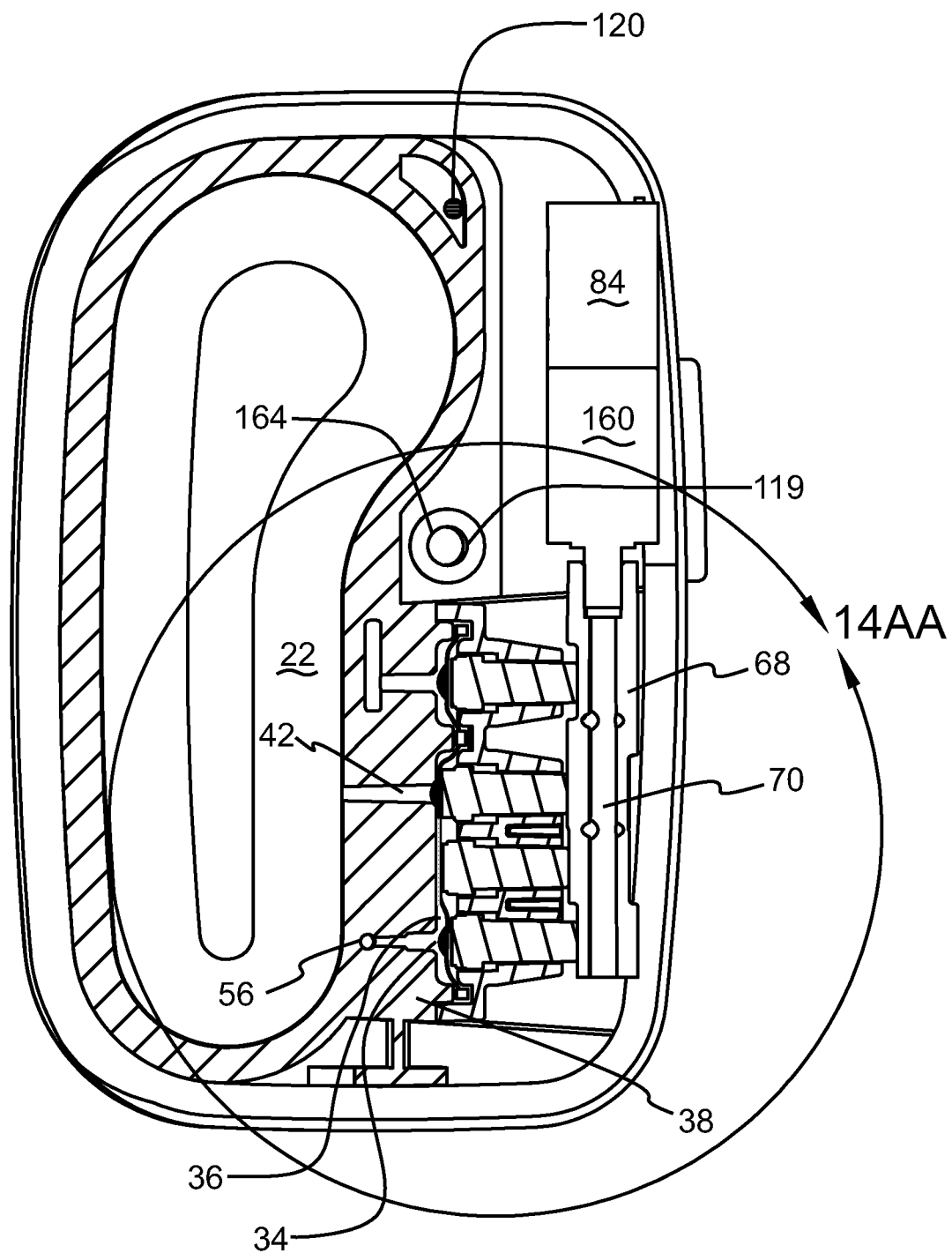
FIG. 14 is a section view of the pump assembly of FIG. 13 taken along lines 14-14 of FIG. 13.
Figure 14A:
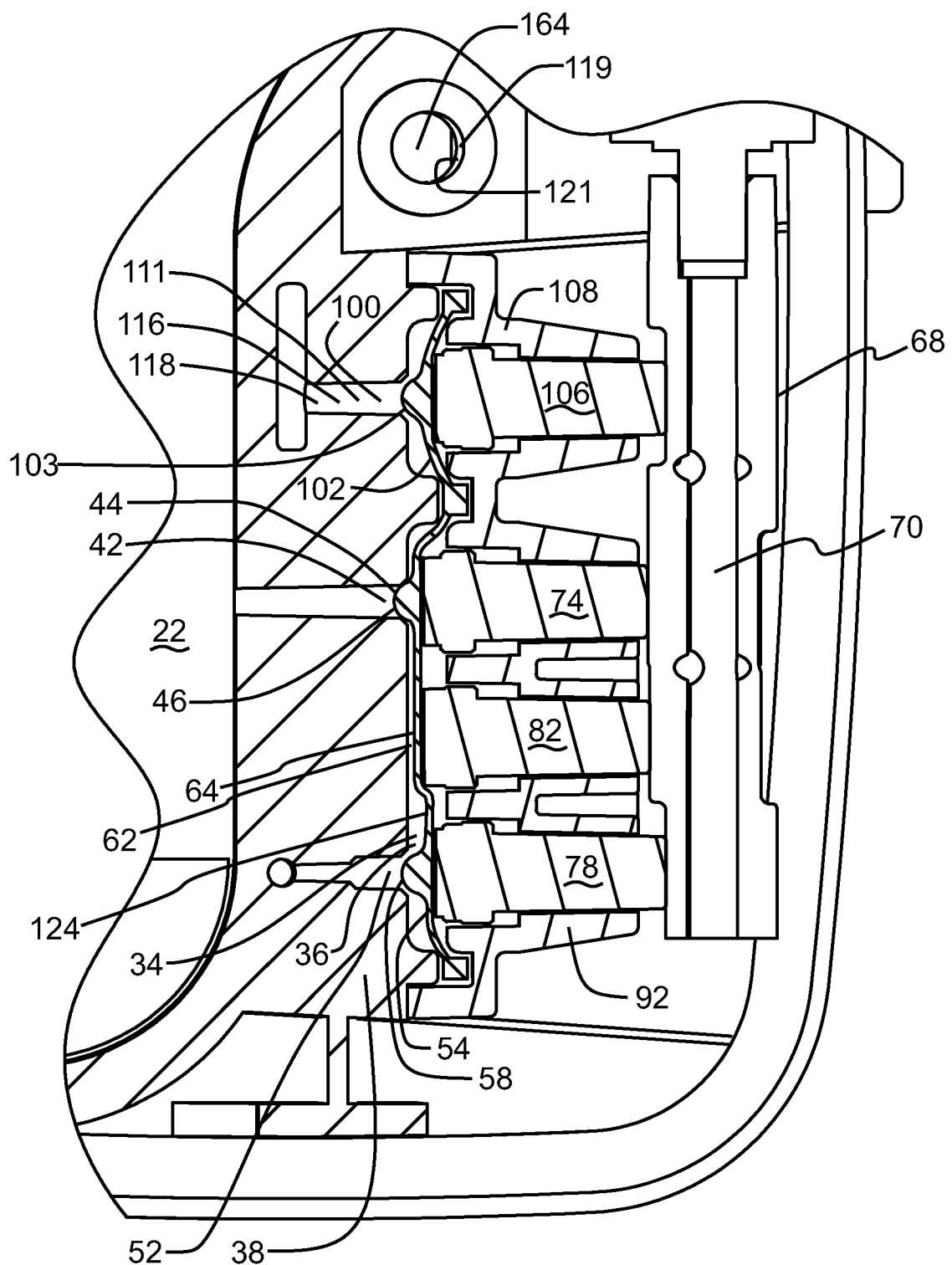
FIG. 14AA is an enlarged view of the reservoir cartridge assembly of FIG. 14 indicated by the encircled portion 14AA-14AA in FIG. 14.
Figure 14A:
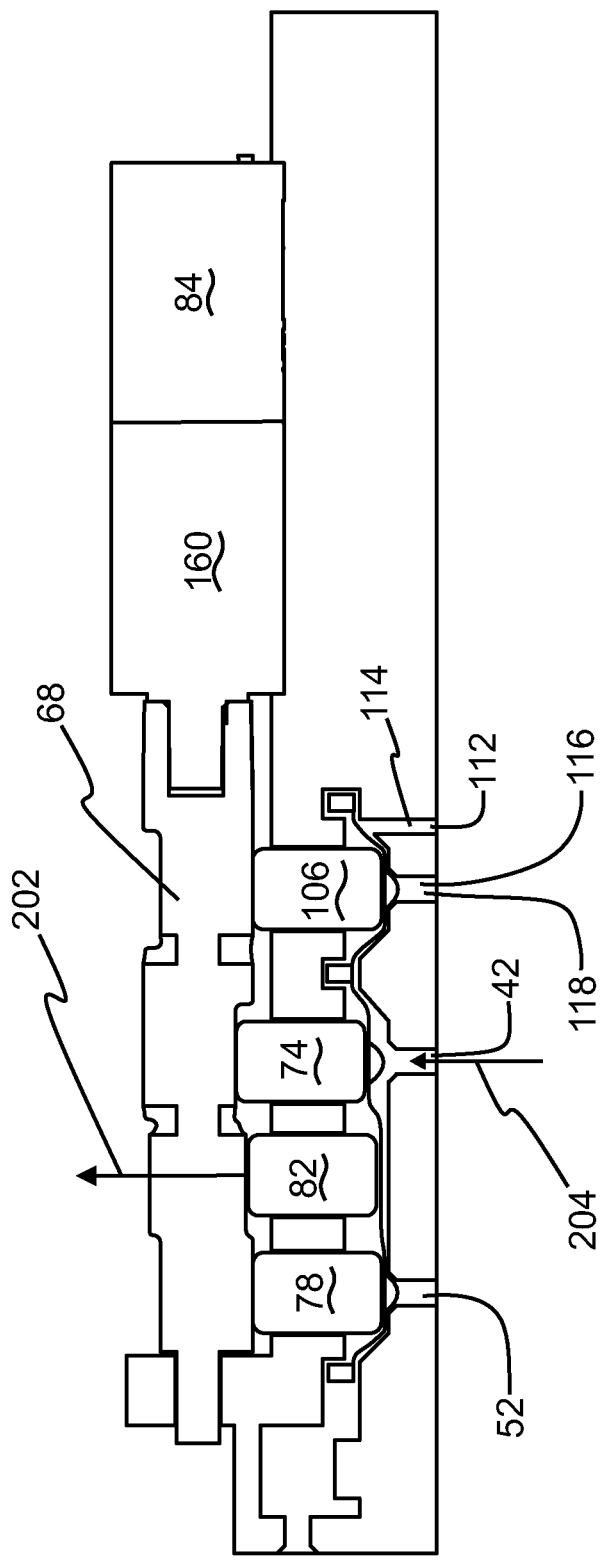

A pump chamber assembly 32, as also seen in FIG. 4, of the reservoir cartridge assembly 12 may include a pump chamber 34, as shown in FIGS. 14 and 14AA, having an interior volume 36 which is at least partially bounded by a pump housing 38. An inlet port 42 of the pump chamber assembly 32 is disposed in fluid communication with the interior volume 36 of the pump chamber 34 and also with the liquid volume 22 of the fluid reservoir 18 which allows therapeutic fluid 50 disposed in the liquid volume 22 of the fluid reservoir 18 to flow into the pump chamber 34 when the inlet port 42 is open. A resilient inlet membrane 44 is disposed adjacent the inlet port 42 and is spaced from the inlet port 42 when in a relaxed state without any external force being applied to it. The resilient inlet membrane 44 is also sufficiently distendable towards the inlet port 42 to seal the inlet port when the resilient inlet membrane 44 is in a compressed state biased towards the inlet port 42. The resilient inlet membrane 44 may also include a dimple 46 that aligned with and disposed towards the inlet port 42 and configured to help seal the inlet port 42 when the resilient inlet membrane 44 is pressed into the inlet port 42.

An outlet port 52 is disposed in fluid communication with the interior volume 36 of the pump chamber 34 and is also disposed in fluid communication with an outlet conduit 56 which allows therapeutic fluid 50 to flow out of the outlet port 52 from the pump chamber 34 when the outlet port 52 is open. A resilient outlet membrane 54 is disposed adjacent the outlet port 52 and is spaced from the outlet port 52 when in a relaxed non-distended state. The resilient outlet membrane 54 is also sufficiently distendable towards the outlet port 52 to seal the outlet port 52 when in a compressed state distended towards the outlet port 52. The resilient outlet membrane 54 may also include a dimple 58 that aligned with and disposed towards the outlet port 52 and is configured to help seal the outlet port 52 when the resilient outlet membrane 54 is pressed against the outlet port 52. A displacement chamber 62 is also disposed within the interior volume 36 of the pump chamber 34. A resilient displacement membrane 64 is disposed adjacent the displacement chamber 62 and forms at least a portion of a boundary of the displacement chamber 62. The resilient displacement membrane 64 is also sufficiently inwardly distendable from a relaxed state to reduce the volume of the displacement chamber 62 when in a compressed state distended inwardly towards the opposite wall of the interior volume 36 of the pump chamber 34. The resilient displacement membrane 64 is also sufficiently resilient to rebound and increase the volume of the displacement chamber 62 when released from the compressed state thereby moving away from the wall opposite the resilient displacement membrane 64. In general, the resilient inlet membrane 44, resilient outlet membrane 54 and resilient displacement membrane 64 may be distended, compressed, and relaxed by the actuation of respective pushrods with valve ends thereof disposed in contact with the resilient membranes 44, 54, 64 discussed in more detail below.

Figure 5:
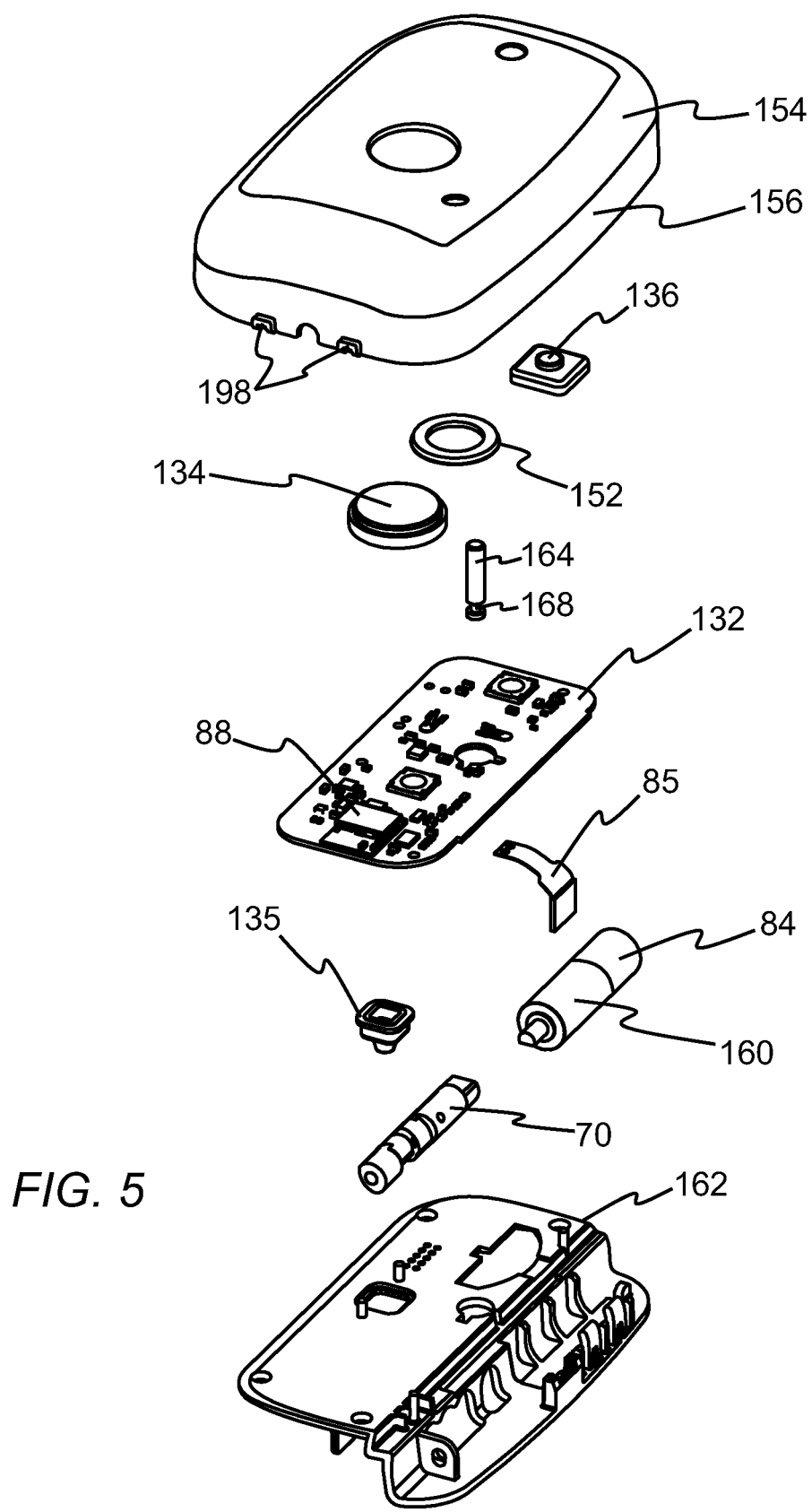
FIG. 5 is an exploded view of an actuator assembly embodiment of the medical pump system embodiment of FIG. 2.
Figure 6:
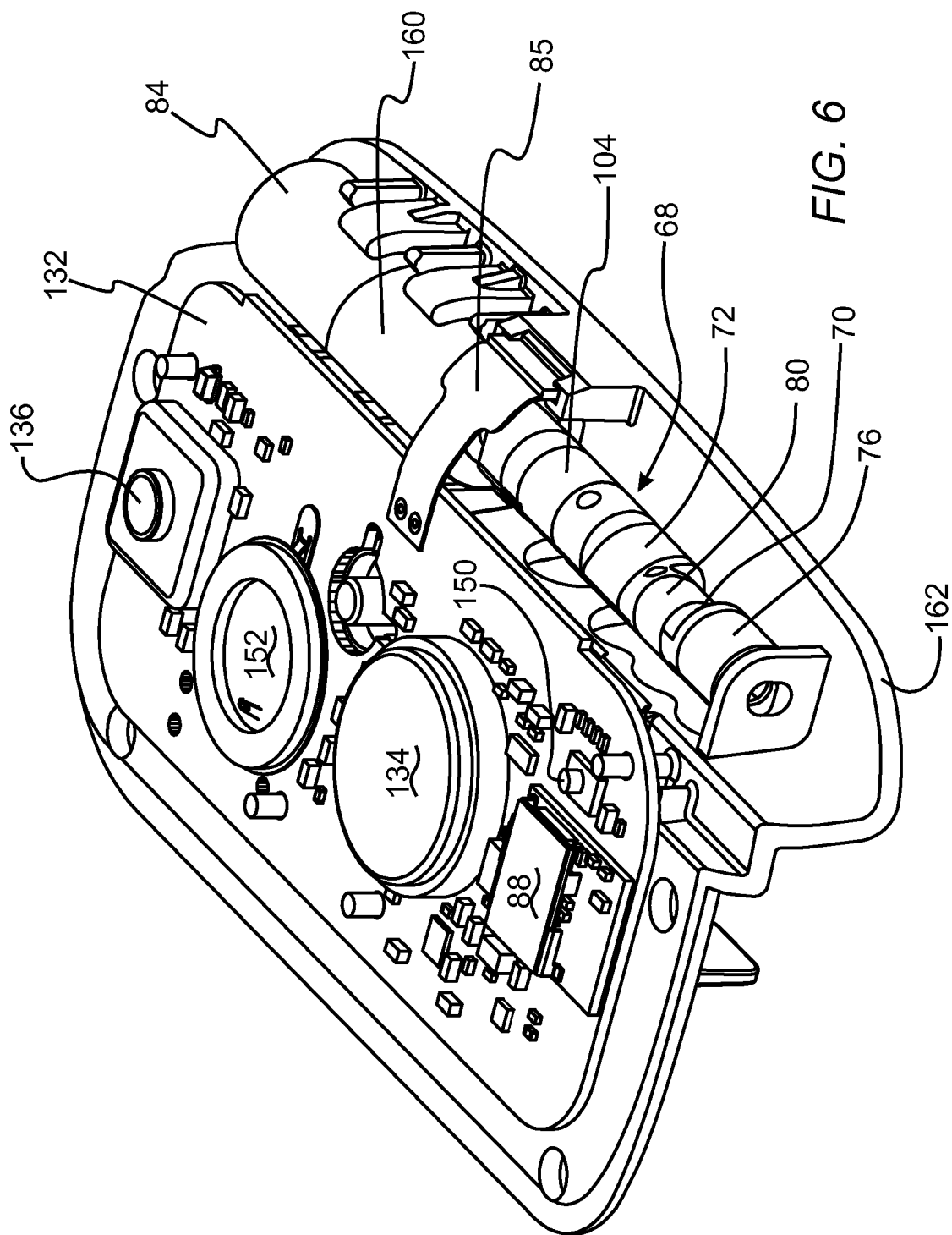
FIG. 6 is a perspective view of the actuator assembly embodiment of FIG. 5 shown without the outer shell for purposes of illustration.

The pushrods in contact with the various resilient membranes 44, 54, 64 of the pump chamber assembly 32 may be actuated by a cam assembly 68 of the actuator assembly 14. For some embodiments, the actuator assembly 14 may be configured to be operatively and releasably coupled to the reservoir cartridge assembly 12 as noted above. Embodiments of the actuator assembly 14 may include the cam assembly 68 which may have a cam shaft 70 with an inlet cam lobe 72 which is operatively coupled to the resilient inlet membrane 44, an outlet cam lobe 76 which is operatively coupled to the resilient outlet membrane 54, and a displacement cam lobe 80 which is operatively coupled to the resilient displacement membrane 64. The actuator assembly 14 may also include a motor 84 operatively coupled to the cam assembly 68 and a controller 88 operatively coupled to the motor 84. In some cases, the motor 84 may be coupled to the controller 88 with a flexboard assembly conduit 85 as seen in FIG. 5.

For some embodiments, the reservoir cartridge assembly 12 may further include an inlet pushrod 74 which is operatively disposed between the inlet cam lobe 72 and the resilient inlet membrane 44, an outlet pushrod 78 operatively disposed between the outlet cam lobe 76 and the resilient outlet membrane 54 and a displacement pushrod 82 operatively disposed between the displacement cam lobe 80 and the resilient displacement membrane 64. A pushrod guide 92 may be secured to a reservoir base 94 of the reservoir cartridge assembly 12. Such a pushrod guide may include a rigid configuration with an inlet pushrod bore disposed about and guiding the inlet pushrod 74, a displacement pushrod bore disposed about and guiding the displacement pushrod 82 and an outlet pushrod bore disposed about and guiding the outlet pushrod 787. Regarding the respective inlet and outlet valve assemblies discussed above, a combination of the inlet port 42, resilient inlet membrane 44, inlet pushrod 74 and associated portion of the pushrod guide 92 may be said to form an inlet valve assembly 75. A combination of the outlet port 52, resilient outlet membrane 54, outlet pushrod 78 and associated portion of the pushrod guide 92 may be said to form an outlet valve assembly 79. In addition, with regard to this configuration, the resilient inlet membrane 44 may be said to be operatively coupled to the inlet cam lobe 72 by the inlet pushrod 74, the resilient outlet membrane 54 may be said to be operatively coupled to the outlet cam lobe 76 by the outlet pushrod 78, and the resilient displacement membrane 64 may be said to be operatively coupled to the displacement cam lobe 80 by the displacement pushrod 82.

Figure 14C:
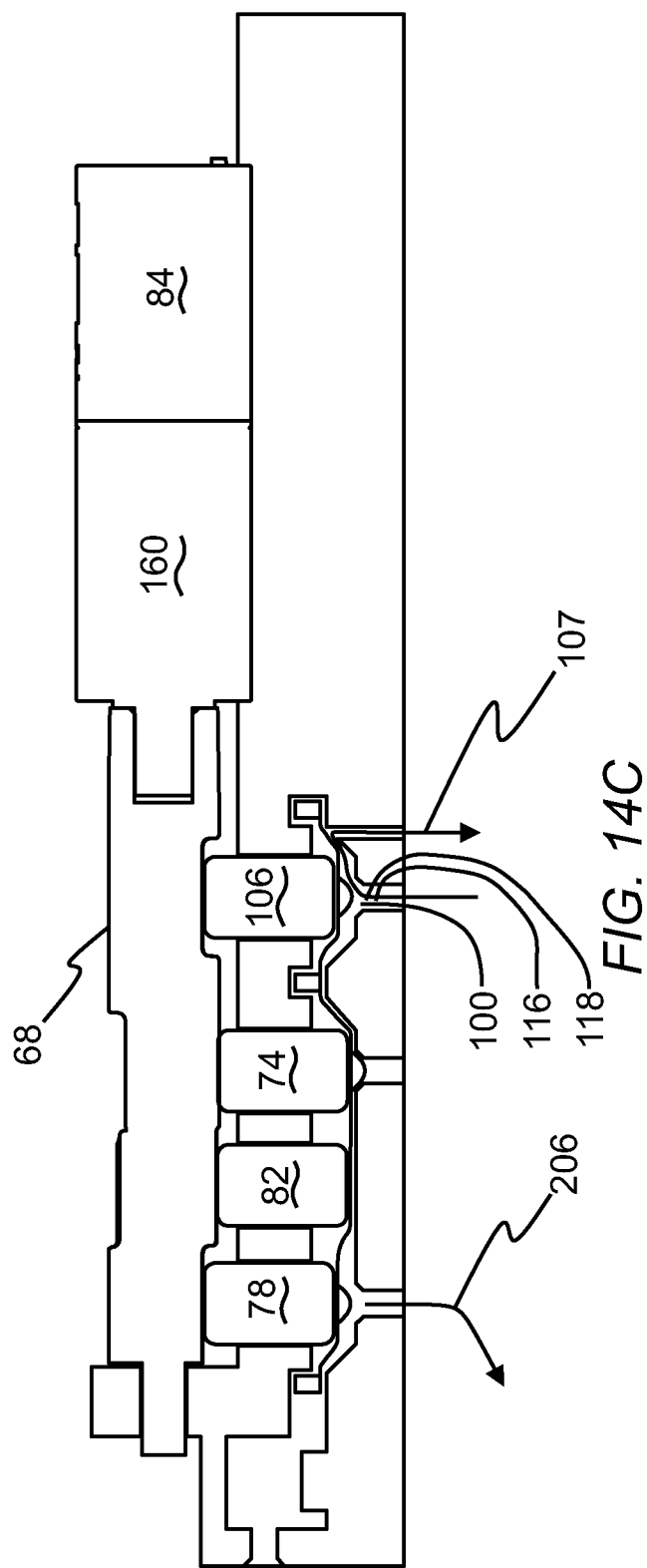

In some cases, the reservoir cartridge assembly 12 may further include a vent port 100 and a resilient vent membrane 102 which is disposed adjacent the vent port 100 and which is also spaced from the vent port 100 when in a relaxed state as shown in FIG. 14AA. The resilient vent membrane 102 is also sufficiently distendable towards the vent port 100 to seal the vent port 100 when the resilient vent membrane 102 is in a compressed state distended towards the vent port 100. In addition, the cam assembly 68 may further include a vent cam lobe 104 which is operatively coupled to the resilient vent membrane 102 by a vent pushrod 106 which is operatively disposed between the vent cam lobe 104 and the resilient vent membrane 102. In addition, a vent pushrod guide portion 108 of the pushrod guide 92 may be secured in fixed relation to the pump housing 38 and include a vent pushrod bore 110 disposed about and guiding the vent pushrod 106. A combination of the vent port 100, resilient vent membrane 102, vent pushrod 106 and vent pushrod guide portion 108 may be said to form a vent valve assembly 109. The resilient vent membrane 102 may also include a dimple 103 that is aligned with and disposed towards the vent port 100 and configured to help seal the vent port 100 when the resilient vent membrane 103 is pressed into the vent port 100. In some cases, the state of the vent valve assembly 109 may determine whether the air volume 24 of the fluid reservoir 18 is vented to the ambient atmosphere or not. In particular for some embodiments, if the vent port 100 of the vent valve assembly 109 is closed, as shown in FIG. 14A, then the air volume 24 is not vented to the ambient atmosphere outside of the medical pump system 10. If the vent port 100 of the vent valve assembly 109 is open, as shown in FIG. 14C, then the air volume 24 is vented to the ambient atmosphere through the vent valve assembly 109 as indicated by the arrow 107. As such, the vent valve assembly 109 acts as a gateway for a vent conduit pathway 111 that extends from the air volume 24 to the ambient atmosphere disposed outside the medical pump system 10.

Figure 8:
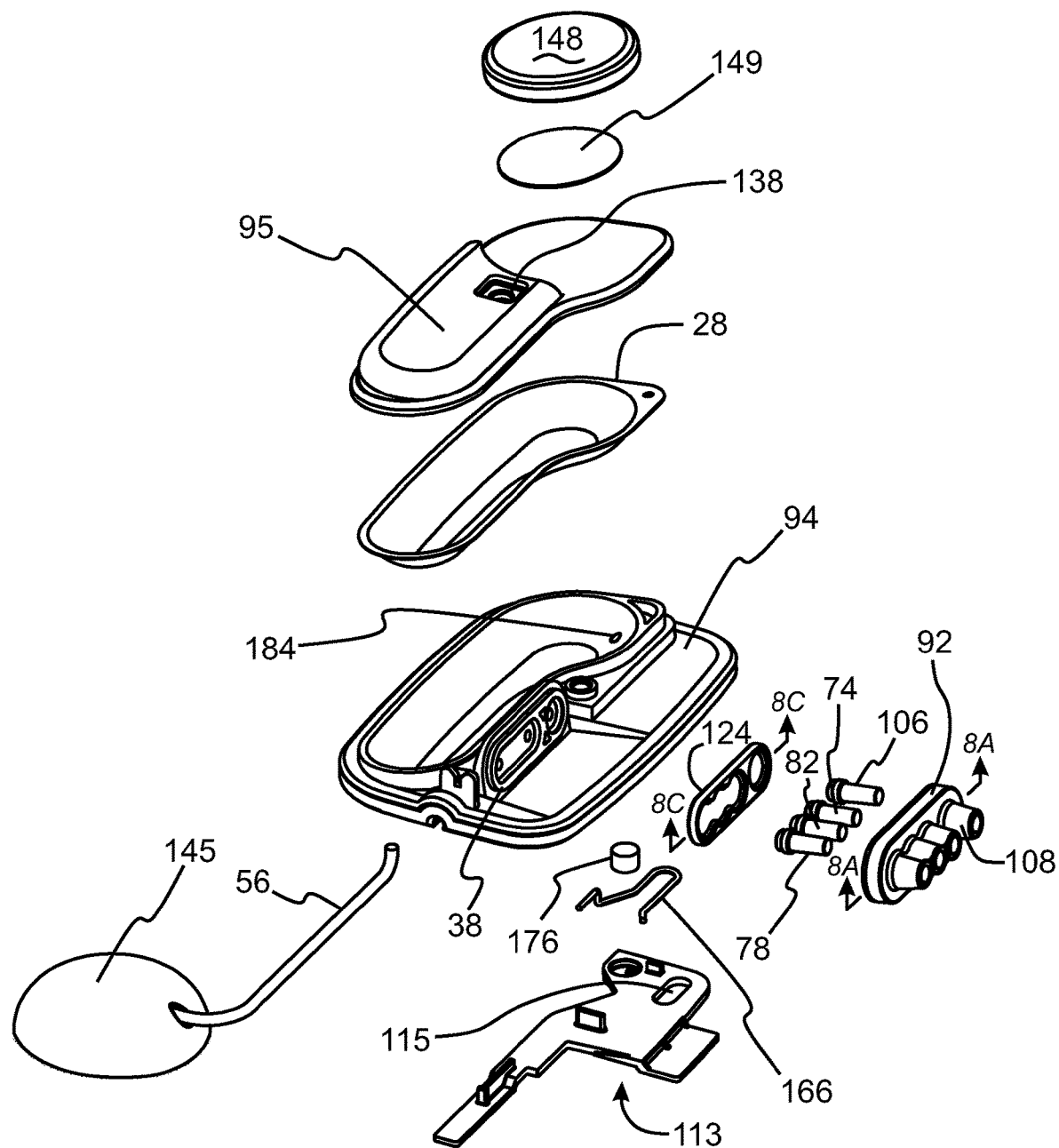
FIG. 8 is an exploded view of a reservoir cartridge embodiment of the medical pump system embodiment of FIG. 2.
Figure 8A:
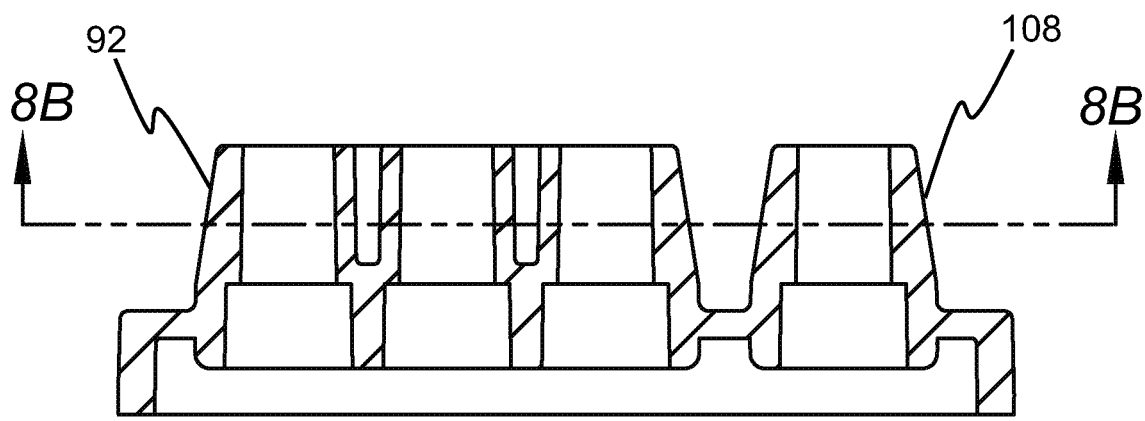
FIG. 8A is an elevation view in longitudinal section of a pushrod guide of FIG. 8 taken along lines 8A-8A of FIG. 8.
Figure 8B:
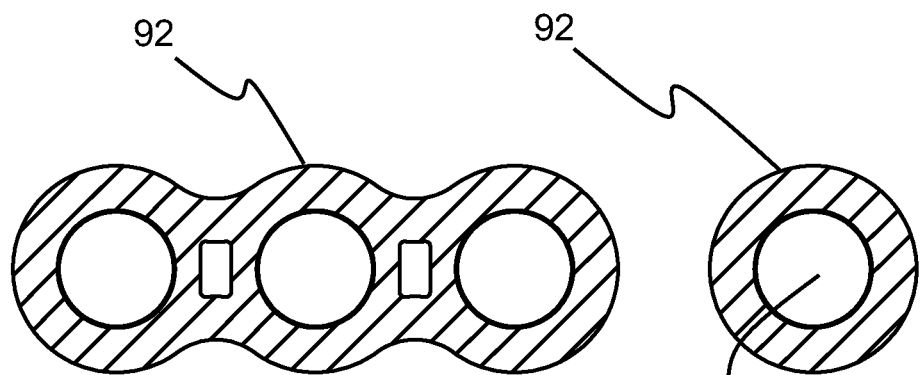
FIG. 8B is a transverse section of the pushrod guide of FIG. 8A taken along lines 8B-8B of FIG. 8A.
Figure 8C:
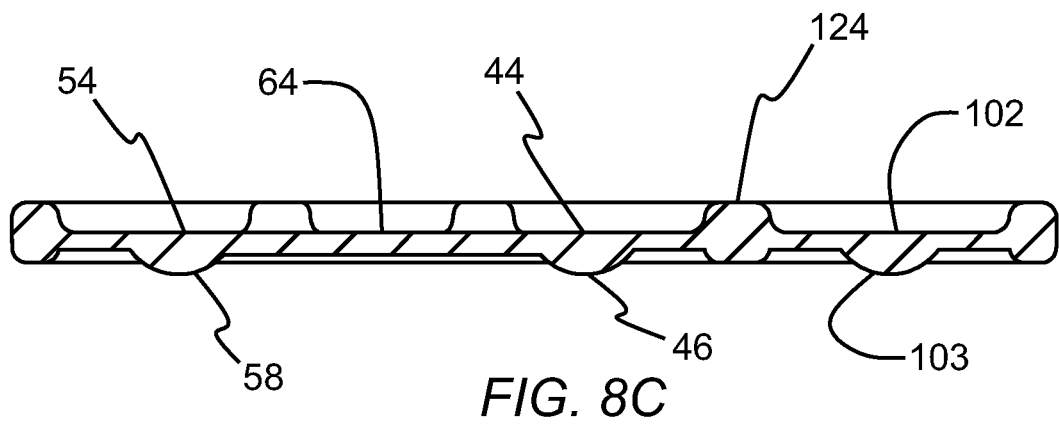
FIG. 8C is a longitudinal section of a continuous pump membrane embodiment of FIG. 8 taken along lines 8C-8C of FIG. 8.

For some embodiments, the pushrod guide 92 and pushrod bores disposed therein may be configured such that longitudinal axes of the respective pushrod bores, including the inlet pushrod bore, outlet pushrod bore, displacement pushrod bore and vent pushrod bore, are all parallel to each other and may also all lie in a common plane as shown in the embodiment of FIGS. 8, 8A and 8B. As such, the pushrods associated with this configuration, including the inlet pushrod 74, outlet pushrod 78, displacement pushrod 82 and vent pushrod 106, may also have respective longitudinal axes that are all parallel to each other and lie in a common plane when assembled in the pushrod guide 92. The pushrods including the inlet pushrod 74, outlet pushrod 78, displacement pushrod 82 and vent pushrod 106, may have a generally cylindrical configuration with a flanged portion disposed at an inward end of the pushrod. The flanged portion may extend radially outward so as to be mechanically captured by a corresponding expanded section of each respective pushrod bore, with each expanded section also being disposed at the inward end of the pushrod guide 92. In such cases, the flanged portion of each pushrod may be small enough to fit and slide easily within the expanded section of its respective pushrod bore, but too large in transverse dimension to fit into the nominal bore. The axial length of the expanded section of each pushrod bore may be sufficiently greater than an axial length of each respective flanged portion such that each pushrod which is slidingly disposed within its pushrod bore of the pushrod guide 92 is configured to slide in an axial direction within the pushrod bore over a limited axial range determined by the axial length of the expanded section. For this linearly oriented configuration, the associated pump chamber 34 may also be similarly configured with the shallow elongate interior volume 36 of the pump chamber 34 having the inlet port 42, displacement chamber 62 and outlet port 52 lying along a line with the displacement chamber 62 disposed between the inlet port 42 and outlet port 52. For some embodiments, the pump chamber 34 may be configured as a shallow rectangular shape with radiused ends bounded on one side by the pump chamber housing 38 and on the other side by the resilient continuous pump membrane 124 as seen in FIG. 8C. The inlet port 42 and outlet port 52 are formed into the pump chamber housing 38. Other such pump chamber embodiments 34 may also have other suitable configurations wherein the inlet port 42, outlet port 52 and displacement chamber 62 do not all lie along the same line, nor would the associated resilient membranes and associated pushrods. The linear configuration of the embodiment shown may be useful for pump assemblies that utilize a single linear cam shaft 70 that includes the multiple lobes associated with each portion of the pump chamber 34 and/or vent valve assembly 109.

Figure 12:
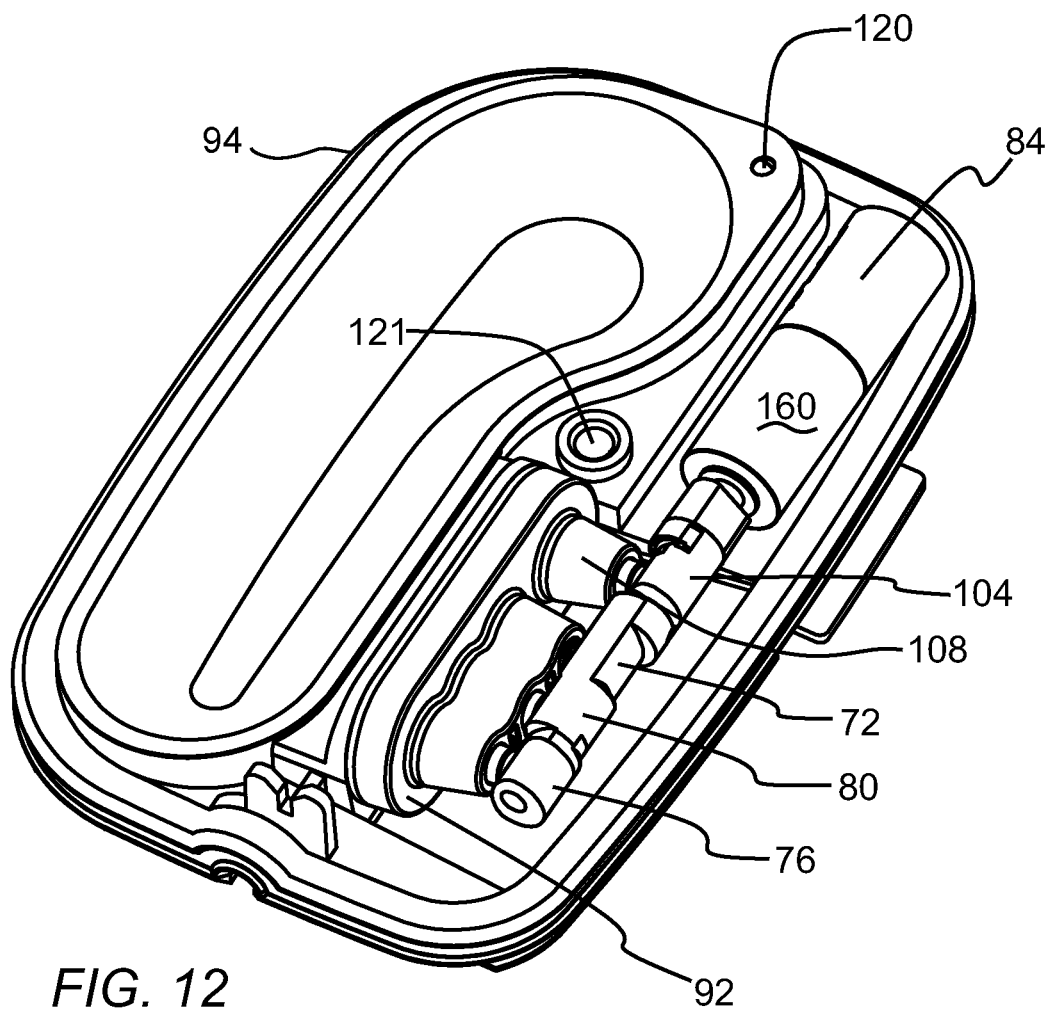
FIG. 12 is a top view in perspective of a subassembly including a reservoir base embodiment of the reservoir cartridge assembly and a cam shaft and drive train embodiment of the actuator assembly with the cam shaft of the actuator assembly operatively coupled to the pushrods of the reservoir cartridge assembly.
Figure 13:
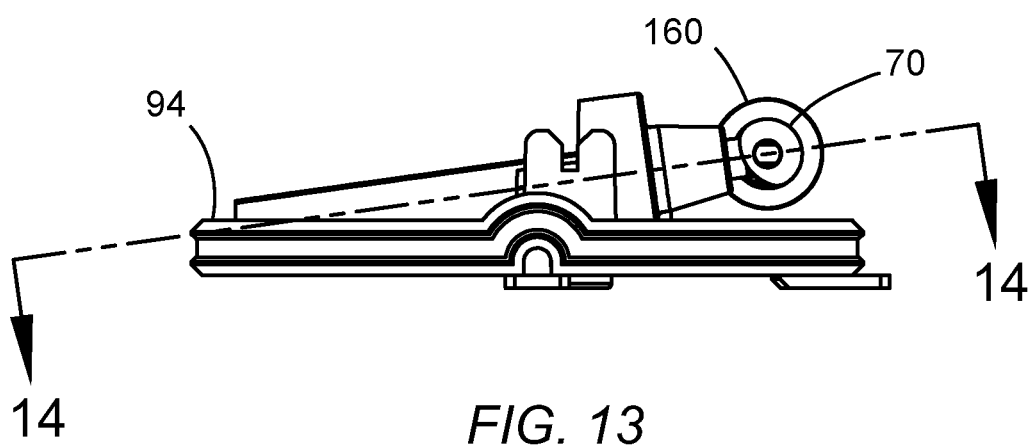
FIG. 13 is a side view of the subassembly of FIG. 12.

For some embodiments, the vent valve assembly 109, and particularly an inner volume thereof, may be disposed in fluid communication with an outlet end 116 of a pre-valve vent conduit 118 of the vent conduit pathway 111 as shown in FIGS. 14A-C, and 19A-B. The pre-valve vent conduit 118 extends from the vent valve assembly 109 to an inlet end 120 of the pre-valve vent conduit 118 as shown in FIGS. 12 and 14, with the inlet end 120 being disposed adjacent and in fluid communication with the air volume 24 of the fluid reservoir 18. The pre-valve vent conduit 118 extends through the reservoir cartridge assembly 12 through a channel formed by a slot in the reservoir base 94 that is sealed on a bottom side thereof by an upper surface of a latch spring cover plate 113 as shown in FIGS. 8, 18, 19A and 19B. The latch spring cover plate 113 also includes a latch release slot 115 that provides limited access for release of the latch spring 166 discussed in more detail below. The latch release slot 115 may also serve as the final access point to ambient atmosphere for the vent conduit pathway 111.

The vent valve assembly 109, and particularly the inner volume thereof, may also be disposed in fluid communication with an inlet end 112 of a post-valve vent conduit 114 of the vent conduit pathway 111, as shown in FIGS. 14A-B and 19A-B. The post-valve vent conduit 114 is also in fluid communication with the ambient atmosphere that surrounds the medical pump system 10 at an outlet end 117 thereof. The vent path of the post-valve vent conduit 114 begins at the inlet end 112 adjacent the vent valve assembly 109 and then vents into an interior volume space disposed between the reservoir cartridge assembly 12 and the actuator assembly 14, this interior volume space being sealed around a perimeter thereof as discussed in more detail below. The vent path then continues to an air gap 119 disposed between an outside surface of a latch post 164 that is secured to an actuator chassis 162 and a latch post bore 121 disposed in the reservoir base 94 of the reservoir cartridge assembly 12. The latch post 164 and latch post bore are components of the latch mechanism 16 discussed in more detail below. The air gap 119 and latch post bore 121 are shown in FIGS. 8, 12, and 14AA. The vent path then continues from the air gap 119 to the latch release slot 115 disposed on the bottom of the reservoir cartridge assembly 12 and then out to ambient atmosphere. For embodiments such as these, the latch release slot 115 may serve as the outlet end 117 of the post-valve vent conduit 114. The tortuous nature of the vent conduit pathway 111 that includes the pre-valve vent conduit 118 and the post-valve vent conduit 114 may be useful in some circumstances in order to reduce the intrusion of contaminants into the vent conduit pathway 111 as well as the vent valve assembly 109 and air volume 24. In addition, as the vent conduit pathway 111 is included within the reservoir cartridge assembly 12, which may, in some cases, be disposable and used for only a limited amount of time, there is also a limited amount of time for contaminants such as dust, moisture etc. to accumulate in the vent conduit pathway 111.

In some cases, a single continuous pump membrane 124, as shown in FIGS. 8, 8C and 14AA, may be configured to be elastically resilient and to include the resilient inlet membrane 44, resilient displacement membrane 64, and resilient outlet membrane 54. In some instances, this single continuous pump membrane 124 may also include the resilient vent membrane 102. Although, in some cases, each of the inlet cam lobe 72, outlet cam lobe 76, displacement cam lobe 80 and vent cam lobe 104 may be actuated by a separate cam and motor mechanism, in general the inlet cam lobe 72, outlet cam lobe 76, and displacement cam lobe 80 may be disposed on the cam shaft 70 which may have a continuous unitary configuration wherein all of the cam lobes disposed thereon are secured in fixed relation to each other and rotate together. In addition, for some such integrated cam shaft embodiments 70, the vent cam lobe 104 may also be included and disposed in fixed relation to the inlet cam lobe 72, outlet cam lobe 76 and displacement cam lobe 80 and rotate together with those cam lobes. For this type of unitary cam configuration, the inlet cam lobe 72, outlet cam lobe 76 and displacement cam lobe 80 may be configured and phased to generate a pumping cycle with each rotation of the cam shaft, with each pumping cycle including a fill cycle of the pump chamber 34 that includes opening the inlet port 42 while the outlet port 52 is closed, expansion of the displacement chamber 62 while the inlet port 42 is open and then closing the inlet port 42 when the displacement chamber 62 is full of therapeutic fluid 50 while the outlet port 52 is still closed. When the displacement chamber 62 is full and the inlet port 42 and outlet port 52 are both closed, the pup chamber assembly 32 may be said to be in a pre-dispense state.

To carry out this fill cycle, as the cam shaft 70 is being rotated, opening the inlet port 42 includes retracting a contact surface of the inlet cam lobe 72 and associated inlet pushrod 74 to allow the resilient inlet membrane 44 to relax away from the inlet port 42. The outlet port 52 is closed due to the extension of a contact surface of the outlet cam lobe 76 against a cam end of the outlet pushrod 78 which in turn distends the resilient outlet membrane 54 against the outlet port 52 so as to close the outlet port 52. In this case, with the inlet port 42 in an open state, the outlet port 52 in a closed state, and the displacement chamber 62 in a minimum volume state, the pump chamber assembly may be said to be in a pre-fill stage of a pumping cycle. For the next step, the displacement chamber 62 may expanded by retracting a contact surface of the displacement cam lobe 80 and thereby retracting the associated displacement pushrod 82 to allow the resilient displacement membrane 64 to rebound and expand the effective volume of the displacement chamber 62 thus carrying out the fill cycle. For some embodiments, the amount of time for filling the displacement chamber may be about 10 seconds to about 30 seconds or more. In some cases, the displacement chamber 62 may be filled during a fill cycle over a period of about 12 seconds to about 20 seconds or more.

The contact surface of each of the respective cam lobes 72, 76, 80, 104 is that part of the cam lobe that is in contact with the respective pushrod. As such, the respective contact surfaces move around each of the cam lobes as the cam shaft is rotated. It should be noted that in some cases, each of the resilient membranes 44, 54, 64, 102 may be configured such that they are continually applying back pressure to the respective pushrods such that the pushrods are always exerting some pressure against the cam lobes without any lash therebetween. This same arrangement is also present for the single continuous pump membrane embodiment 124 that includes each of the resilient inlet membrane portion 44, resilient outlet membrane portion 54, resilient displacement membrane portion 64 and resilient vent membrane portion 102.

With regard to certain use embodiments of the pump chamber assembly 32 of the medical pump system 10, for some embodiments the inlet cam lobe 72, outlet cam lobe 76 and displacement cam lobe 80 may be configured and phased to generate a dispense cycle that includes opening the outlet port 52 while the inlet port 42 is closed, compression of the displacement chamber 62 while the outlet port 52 is open and closing of the outlet port 52 while the inlet port 42 is still closed. In some cases the inlet cam lobe 72, outlet cam lobe 76 and displacement cam lobe 80 may be configured and phased such that the inlet port 42 and outlet port 52 are never open at the same time during a complete rotation of the cam shaft 70. As such, prior to the initiation of this dispense cycle, the inlet valve 42 is typically closed prior to opening of the outlet valve 52 such that the pump chamber assembly 32 is in a pre-dispense state with the dispense chamber 62 full of therapeutic fluid 50 and both the inlet valve 42 and outlet valve 52 in a closed state. For some pump assembly embodiments of the medical pump system 10 the volume and configuration of the pump chamber 34 and the lift and duration of the inlet cam lobe 72, outlet cam lobe 76 and displacement cam lobe 80 may be configured to deliver about 2 microliters to about 10 microliters, more specifically, about 4 microliters to about 6 microliters, of therapeutic fluid 50 from the outlet port 52 for each pumping equivalent to one rotation of the cam shaft 70.

With regard to a venting function wherein the vent port 100 is opened to ambient atmosphere such that the air volume 24 of the fluid reservoir 18 is thereby vented to ambient atmosphere through the open vent port 100, in some cases the inlet cam lobe 72, outlet cam lobe 76 and vent cam lobe 104 may be configured and phased such that the vent port 100 is open while the outlet port 52 is open and the inlet port 42 is closed. In some cases, the inlet cam lobe 72, outlet cam lobe 76 and vent cam lobe 104 may be configured and phased such that the vent port 100 is open while the cam shaft 70 is paused after a dispense cycle and before the beginning of a fill cycle. When the vent port 100 is open to ambient atmosphere, a pressure sensor 130 disposed on the actuator assembly 14 and disposed in fluid communication with the air volume 24 of the liquid reservoir 18 is also exposed to the ambient atmosphere and is thereby configured to monitor the pressure of the ambient atmosphere and sense any changes in the ambient atmospheric pressure during this period.

The pressure sensor 130 may also be configured to determine a remaining volume of therapeutic fluid 50 disposed in the liquid volume 22 of the fluid reservoir 18 by measuring small pressure drops in the air volume 24 during a dispense cycle. Certain embodiments of the pressure sensor 130 may also include temperature measurement capabilities. For some embodiments, such a pressure sensor 130 may include a software controlled, high performance MEMS nano-pressure sensor having a measurement range of about 260 hPA to about 1260 hPA absolute pressure and a temperature measurement range of about −40 degrees F. to about 180 degrees F.

Figure 15:
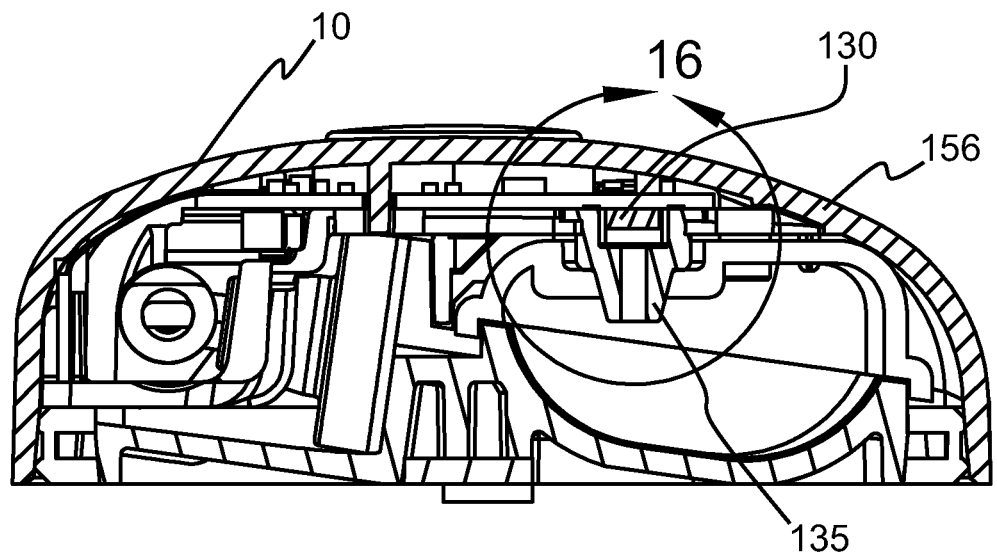
FIG. 15 is a transverse cross section view of the medical pump system embodiment of FIG. 2.
Figure 16:
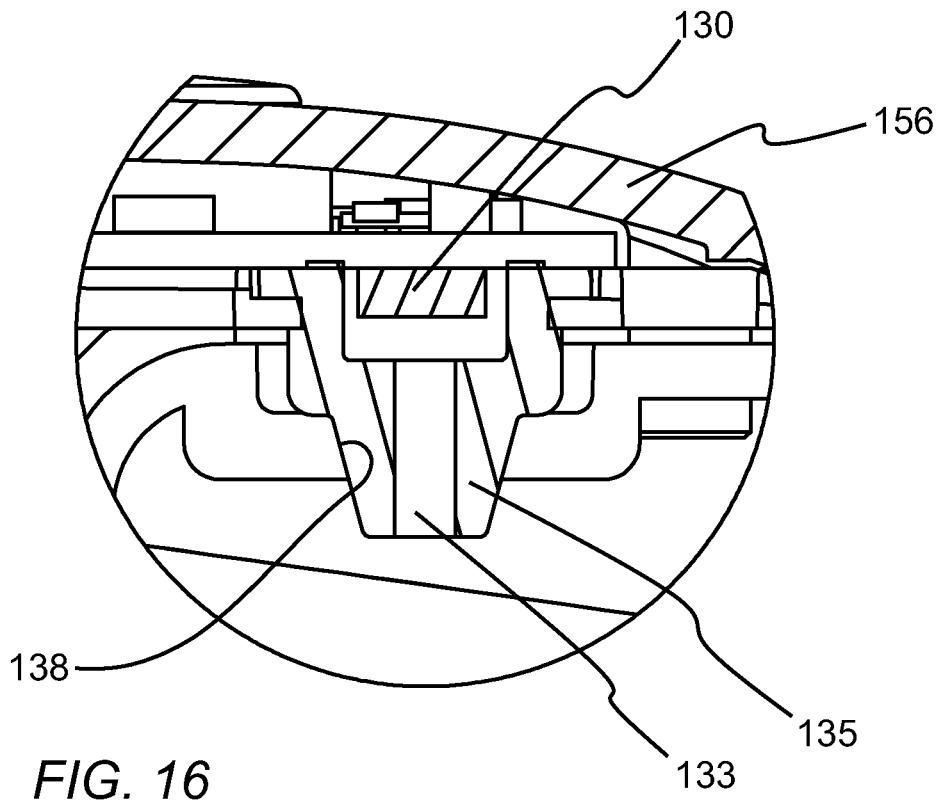
FIG. 16 is an enlarged view of the medical pump system embodiment of FIG. 15 indicated by the encircled portion 16-16 of FIG. 15.

Because such pressure sensor embodiments 130 are preferably reused and not included in the limited use element of the reservoir cartridge assembly 12, it is necessary to establish a reliable sealed fluid communication path between the pressure sensor 130 of the actuator assembly 14 and the air volume 24 of the reservoir cartridge assembly 12. In some cases, the actuator assembly 14 may include a pressure conduit 133 which is disposed in fluid communication with the pressure sensor 130 and the air volume 24 when the actuator assembly 14 and reservoir cartridge assembly 12 are coupled together. For such an arrangement, the actuator assembly may further include a pressure conduit boot 135 which is secured in fluid communication with the pressure conduit 133 and which is configured to sealingly couple to a boot receptacle 138 as shown in FIGS. 15 and 16. The pressure conduit boot 135 may have a generally tapered shape and be made from a compliant elastic material that will readily and sealingly conform to the boot receptacle 138 as shown in FIGS. 15 and 16. The compliant elastic material of the pressure conduit boot 135 may be configured to repeatably and reliably form a seal with boot receptacle embodiments.

For some embodiments, the actuator assembly 14 may include a printed circuit board (PCB) 132 and the controller 88 may be operatively coupled and otherwise secured to the printed circuit board 132. The controller 88 may include a processor 90 such as a microprocessor, memory 91 as well as any suitable components that may be useful for interfacing with the pressure sensor 130, motor 84, user interface embodiments such as a control button 134, priming button 136 and the like. Such components may include electrical contacts, electrical conduits such as wiring, as well as drivers and any other machine-readable instructions stored in the memory 91 that may facilitate use of the medical pump system 10. For some embodiments, the controller 88 may include a "system on a chip" type microprocessor, including a low power consuming high performance microprocessor that may support low energy blue tooth, near field communication and the like such as model nRF52832 manufactured by Nordic Semiconductors located in Trondheim, Norway.

With regard to control of the motor 84 and pump chamber assembly 32, in some cases, the controller 88 may be configured to limit the angular velocity of the cam shaft 70 during a dispense cycle to an angular velocity that will generate a maximum flow of up to about 0.5 microliters per second through a therapeutic fluid dispense circuit of the reservoir cartridge assembly 12. For some embodiments, the angular velocity of the cam shaft 70 may be limited during a dispense cycle to about 0.25 revolutions per minute to about 3 revolutions per minute. Such a limit on flow velocity of the therapeutic fluid 50 through the various conduits of the medical pump system 10 may be useful in maintaining the integrity of the molecular structure of certain therapeutic fluids 50. In addition, in some instances, the controller 88 may be configured to actuate the motor 84 so as to rotate the cam shaft 70 in distinct rotation steps and take pressure measurements within the air volume 24 of the fluid reservoir 18 between the distinct rotation steps. In some cases, the motor 84 may include a direct current (DC) type electric motor that is coupled to the cam shaft 70 through the transmission 160 which provides gear reduction between rotation of the output shaft of the motor 84 and rotation of the cam shaft 70. In some cases, the gear reduction ratio provided by the transmission 160 may be a gear reduction ratio of about 100:1 to about 250:1, more specifically, about 110:1 to about 130:1.

For such an arrangement, the controller 88 may be configured to generate a small pulse of electricity discharged from a capacitor which may be disposed on the PCB 132 which is communicated to the DC input of the motor 84 so as to generate a pulse of rotation in the drive shaft of the motor and a corresponding pulse of rotation, reduced by the gear reduction of the transmission, in the cam shaft 70. In some instances, such pulses of electricity generated by the controller 88 may be about 5 milliseconds to about 50 milliseconds in duration. Such pulses of drive electricity to the motor 84 may generate rotation pulses of the cam shaft 70 of about 3 degrees to about 10 degrees, more specifically, about 5 degrees to about 7 degrees. For some embodiments, the electrical pulses may generate a corresponding rotation pulse of the cam shaft 70 of about 6 degrees such that 60 electrical pulses results in a corresponding 60 rotation pulses of the cam shaft 70 for a total of a 360 degree full rotation of the cam shaft 70. This configuration provides a resolution in the rotation of the cam shaft 70 to the 6 degree value per pulse. In some cases, the controller may be configured to count the number of pulses or steps used per revolution of the cam shaft 70 and utilize an algorithm to adjust the duration of the electrical pulses in order to maintain a rotation per pulse of about 3 degrees to about 10 degrees, more specifically, about 5 degrees to about 7 degrees, and even more specifically, about 6 degrees. For some embodiments, the controller 88 may be configured to rotate the cam shaft 70 one full rotation over a time period of about 15 seconds to about 60 seconds, more specifically, about 25 seconds to about 35 seconds, during normal usage.

Figure 3:
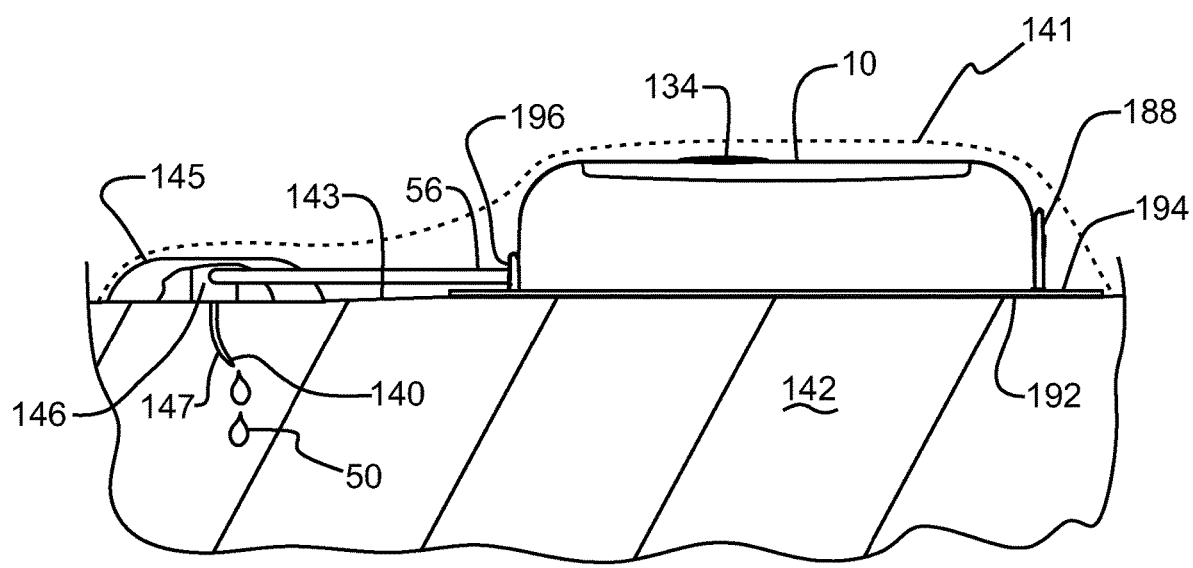
FIG. 3 is an elevation view in partial section of the medical pump system embodiment of FIG. 2 deployed on and releasably secured to a patient's skin with a distal end of a flexible cannula of a patient port disposed in subcutaneous target tissue.

As discussed above, the actuator assembly 14 typically includes the pressure sensor 130 which may be disposed in fluid communication with the air volume 24 of the fluid reservoir 18. The pressure sensor 130 is also operatively coupled to the controller 88 which may be configured to monitor pressure measurements of the pressure sensor 130 from within the air volume 24 of the fluid reservoir 18. The controller 88 may also be configured to trigger an alarm indicating an occlusion in an outlet path 56 between the outlet port 52 and a subcutaneous delivery site 140 within the patient's body 142, as shown in FIG. 3, if an unexpected pressure profile for the air volume 24 is detected by the controller 88 over a plurality of fill cycles, in some cases, if a pressure increase in the air volume 24 is detected over a plurality of consecutive dispense cycles or pumping cycles. In other cases, such an alarm might be triggered if a lack of pressure drop in the air volume 24 is detected during a fill cycle over a plurality of pumping cycles which may be indicative of a lack of flow of therapeutic fluid 50 from the liquid volume 22 during a fill cycle. Such a subcutaneous delivery site 140 may be accessed by deploying a patient port 145 that includes a hub 146 having a flexible tubular cannula 147 extending therefrom as shown in FIG. 3. The hub 146 may be configured to establish fluid communication between an inner lumen of the flexible tubular cannula 147 and the outlet conduit 56 of the medical pump system 10. Any suitable commercially available patient port 145 may be used including an Ypsomed Orbit® Soft Infusion Set manufactured by Ypsomed AG located in Burgdorf, Switzerland.

In some cases, such an alarm may be triggered if such an unexpected pressure profile within the air chamber 24 is detected over about 2 pumping cycles to about 4 pumping cycles. In some cases an occlusion alarm may be triggered by the controller if an increase in pressure in the air chamber 24 is detected over 3 pumping cycles. In some instances, the controller 88 may also be configured to trigger an alarm indicating a pump failure if an unexpected pressure profile for the air volume 24 is detected by the controller 88 over a plurality of fill cycles. In some cases, the controller 88 may be configured to trigger a pump failure alarm if an unexpected pressure profile is detected over about 4 pumping cycles to about 6 pumping cycles. In some circumstances, the controller 88 may be configured to trigger a pump failure alarm if an unexpected pressure profile is detected over about 5 pumping cycles.

With regard to use of the pressure sensor 130, the controller 88 may also be configured to determine the amount of therapeutic fluid 50 disposed in the liquid volume 22 of the fluid reservoir 18 based on a pressure measurement taken from the pressure sensor 130. In some cases, this may be carried out by sensing a magnitude of a pressure drop within the air volume 24 during a fill cycle wherein a predetermined volume of therapeutic fluid 50 is drawn out of the liquid volume 22 and into the pump chamber 34 through the inlet port 42. Typically, a known predetermined volume of therapeutic fluid 50 is dispensed during each pumping cycle. As the therapeutic fluid 50 is withdrawn from the liquid volume 22, the pressure within the liquid reservoir 18 drops. The magnitude of the pressure drop during withdrawal of a predetermined volume of therapeutic fluid 50 may be dependent upon the amount of therapeutic fluid 50 remaining in the liquid reservoir 18 because the therapeutic fluid 50 has little to no compressibility and the air within the fluid reservoir 18 is highly compressible relative to the therapeutic fluid 50.

As such, if the liquid volume 22 is full or nearly full of therapeutic fluid 50, there will be a significantly higher drop in pressure within the liquid reservoir 18 during a fill cycle relative to a drop in pressure if the liquid volume 22 is nearly empty of therapeutic fluid 50 and the liquid reservoir 18 is filled mostly with compressible air. In some cases the actuator assembly 14 may also include a temperature sensor 131 which is disposed in operative communication with the controller 88. This allows the controller 88 to monitor ambient temperature and ambient atmospheric pressure when the vent port 100 is open as well as pressure within the liquid reservoir 22 when the vent port 100 is closed. For some embodiments, the temperature sensor may be part of the pressure sensor 130, i.e., the pressure sensor 130 also includes the temperature sensor.

For some embodiments, the actuator assembly 14 may also include a position sensor 144 which is operatively coupled to the motor 84 and/or the cam shaft 70. The position sensor may further be operatively coupled to the controller 88 thus enabling the controller 88 to monitor the angular position of the motor 84 as well as the cam shaft 70. In some cases, the position sensor 144 may include a microswitch (not shown) having an actuator lever in contact with either a drive shaft of the motor 84 and/or the cam shaft 70. In other cases, the position sensor 144 may include a photo interrupt sensor, a hall effect sensor, a color sensor, an infrared (IR) sensor or the like.

Figure 7:
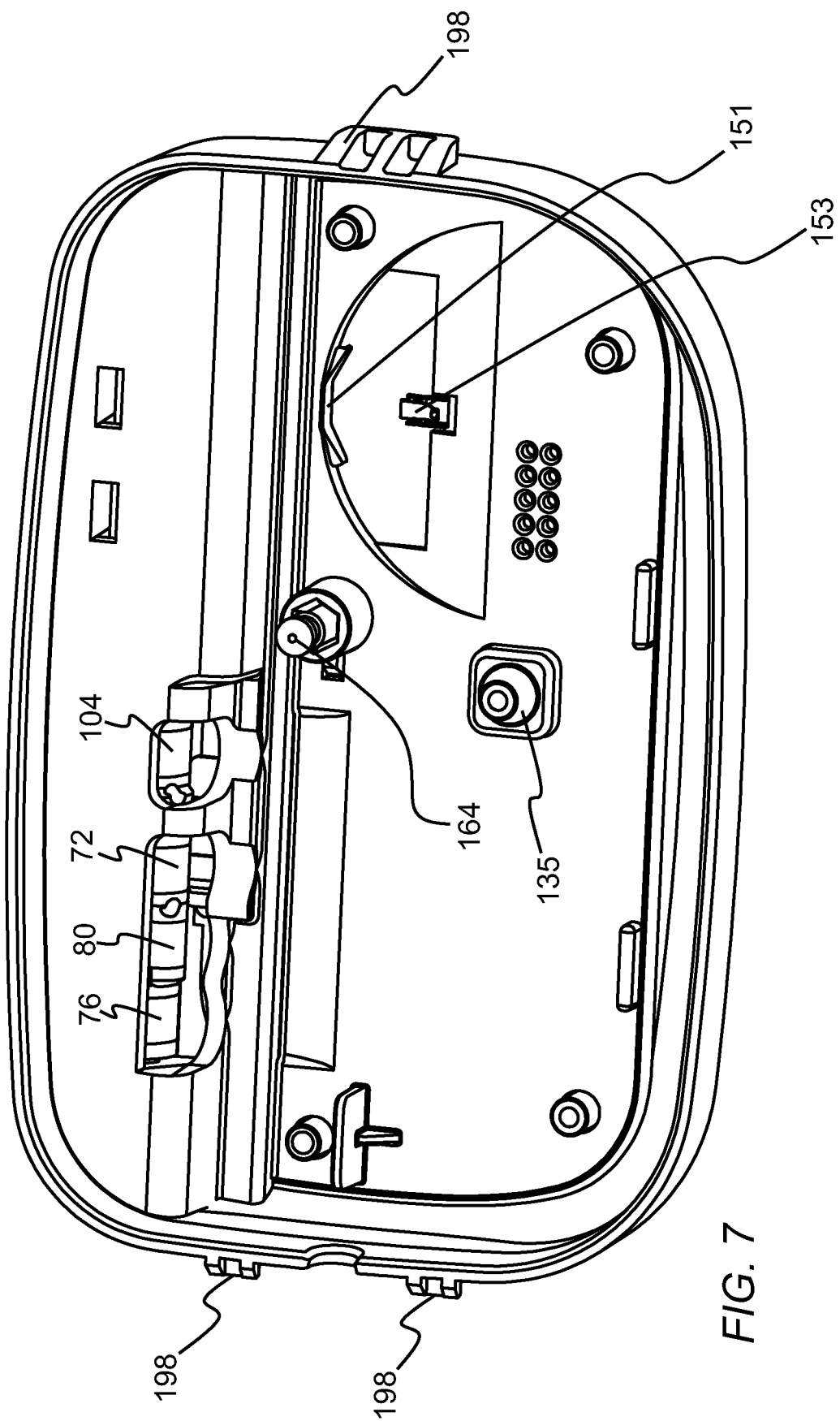
FIG. 7 is a bottom view of the actuator assembly embodiment of FIG. 6.

As the reservoir cartridge assembly 12 is generally configured as limited use element of the medical pump system 10, it may be useful to include components that require frequent refreshing to be included with this assembly 12. In particular, the reservoir cartridge assembly 12 may generally include an electrical power source 148 which may be operatively coupled to the controller 88 with a conductive conduit when the reservoir cartridge assembly 12 and actuator assembly 14 are operatively coupled together. In some cases, the electrical power source 148 may include a battery. In some cases, the battery 148 may also be operatively coupled to the PCB 132 as well. Battery embodiments such as a coin cell type battery, including a CR2032 magnesium dioxide lithium battery, may be suitable for use with the medical pump system embodiments 10 in some cases. For some embodiments, the battery 148 may be secured to a portion of the reservoir cartridge assembly 12 by any suitable means and in some cases the battery 148 may be secured to a top portion of the fluid reservoir cover 95 with a double sided adhesive pad 149 that is secured on one side to the battery 148 and the opposite side to the upper side of the fluid reservoir cover 95. For some embodiments of the battery 148, a negative pole of the battery 148 may be electrically coupled to a first battery contact 151 and a positive pole of the battery may be electrically coupled to a second battery contact 153 as shown in FIG. 7, and the first battery contact 151 and second battery contact 153 may be electrically coupled to the controller 88 and/or PCB 132.

With regard to patient interface features of the medical pump system 10, for some embodiments, the actuator assembly 14 may include an indicator light 150 that is operatively coupled to the controller 88. The indicator light 150 is configured to be viewable by the end user patient and the controller 88 may be configured to communicate a variety of signals to the indicator light 150 indicative of status information regarding the medical pump system 10. In some cases, the indicator light 150 may include a tri-color light emitting diode. The actuator assembly 14 may also include an electronic sound emitter 152 that for some embodiments may include a piezo sounder disc that is audible to a patient and operatively coupled to the controller 88. Any other form of sound emitter 152 may also be so used and operatively coupled to the controller 88 including voice coil speakers and the like. In some instances, the controller 88 may be configured to communicate a variety of signals to the piezo sounder disc 152 which are configured to be converted to corresponding audible signals observable by the patient end user that are indicative of status information regarding the medical pump system 10.

The control button 134 may be disposed coextensively with an outside surface 154 of an outer shell 156 of the actuator assembly 14. The control button 134 may be accessible for manual activation by a patient and operatively coupled to the controller 88 to provide an operative interface between a patient and the controller 88 and its associated control functions and programming. The priming button 136 may also operatively coupled to the controller 88 to provide priming commands to the controller 88 by a patient. In some cases, the controller 88 may be configured to initiate priming of a complete fluid path from the liquid volume 22 of the fluid reservoir 18 to the outlet conduit 56 upon activation of the priming button 136. For some embodiments, the priming button 136 may be recessed into the outside surface 154 of the outer shell 156 of the actuator assembly 14 such that the priming button 136 is not easily accessible for manual activation by a patient without a priming tool (not shown) that may be configured to allow the patient to activate the priming button 136. For some embodiments, the control button 134 may be used by an end user patient to directly control a pumping method of the medical pump system 10.

In some cases, the controller 88, including the memory 91 thereof, may be configured or otherwise include instructions to have certain components of the medical pump system 10 carry out certain processes based on input from the end user patient. For example, for some embodiments, once a steady state infusion rate has been generated by the controller, the patient may use the control button 134 to initiate a bolus delivery of therapeutic fluid 50 to the subcutaneous delivery site 140. In some cases, such a bolus delivery may be instructed by a continuous press of the control button for an intermediate length duration, in some cases this might include a constant three second press of the control button 134. Thereafter, short incremental presses of the control button 134 separated by release of the control button 134 may be used to count out the volume of the bolus to be delivered. The amount of the bolus to be delivered may then be relayed back to the patient by flashes of the indicator light 150 and/or beeps generated by the piezo sounder 152. If these confirmation signals from the indicator light 150 and/or piezo sounder 152 are correct, the patient may then confirm the bolus instruction with a long continuous press of the control button 134, for example, a six second continuous press of the control button 134. Thus, the controller 88 may be configured to deliver a desired volume of bolus delivery using only a single controller button 134 and three types of button presses, including the instantaneous incremental press followed by an immediate release of the control button 134, a continuous press and hold of intermediate length or duration, including the 3 second continuous press and a continuous press and hold of a long duration of about 6 seconds. In some instances, it may be useful for the duration of the long continuous press of the control button 134 to be twice or more that of the intermediate continuous press in order for the patient to be able to easily distinguish between these two types of button presses.

In some cases, the controller 88 and associated components thereof may be configured such that an in progress bolus delivery may be canceled by a long duration continuous press of the control button 134. In addition, the controller 88 and associated components thereof may be configured such that an in progress controlled infusion rate, such as a basal rate, delivery may be canceled by a long duration continuous press of the control button 134. In addition, during normal operation of some medical pump system embodiments 10, a status check may be initiated by the patient by a single short press of the control button 134 followed by immediate release. The short press and release of the control button 134 may also be used to acknowledge any alerts being transmitted by the controller 88 through the piezo sounder 152 and/or indicator light 150.

For some embodiments, the actuator assembly 14 may include an optional transmission 160 which is operatively coupled between the cam assembly 68 and the motor 84. For some motor embodiments, such a transmission 160 may not be necessary. However, for some motor embodiments 84, it may be useful to include such a transmission 160 in order to better control rotation of the cam shaft 70 with a suitable gear reduction ratio. In some cases, the transmission 160 may include a planetary gear box or the like.

Figure 17:
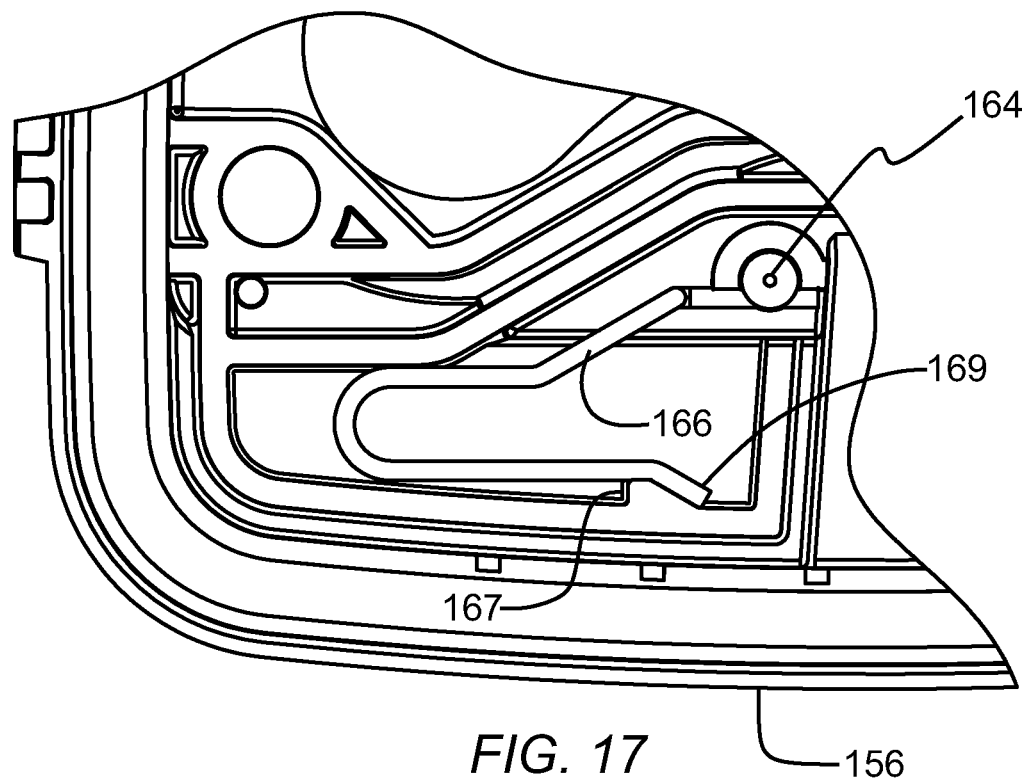
FIG. 17 is an enlarged bottom view partially cut away of the reservoir cartridge assembly embodiment and showing a latch spring embodiment thereof.

Some embodiments of the actuator assembly 14 may include an actuator chassis 162 and the cam assembly 68, motor 84 and transmission 160 may be disposed on the actuator chassis 162. The actuator assembly 14 may also include a latch post 164 secured to and extending from a bottom surface of the actuator chassis as shown in FIG. 7. The reservoir cartridge assembly 12 may in turn include a latch spring 166 that is disposed on the reservoir base 94 of the reservoir cartridge assembly 12 as shown in FIGS. 7 and 17. The latch spring 166 may be configured to latch onto a groove or slot 168 the latch post 164, as shown in FIG. 5, to prevent separation of the actuator assembly 14 from the reservoir cartridge assembly 12 after they have been operatively coupled together. In some instances, the latch spring 166 may be configured to be permanently disabled after being disengaged from a latch post 164 to prevent multiple uses of the latch spring 166. As such, the latch mechanism 16 may include a disabling feature 167, shown in FIG. 17, which the latch spring 166 is spring biased against and which includes a ramped end and a flat end. When the latch spring 166 is disengaged by translating the latch spring 166 to the left with the priming tool or any other suitable instrument, the biased end 169 of the latch spring 166 slides up and over the ramp end and elastically snaps into engagement behind the flat end with the latch spring in a position where it no longer is able to engage the groove 168 of the latch post 164, thus disabling the latch mechanism embodiment 16. The disabling feature 167 shown in FIG. 17 is an exemplary embodiment and any other suitably configured mechanism may also be used.

Figure 9:
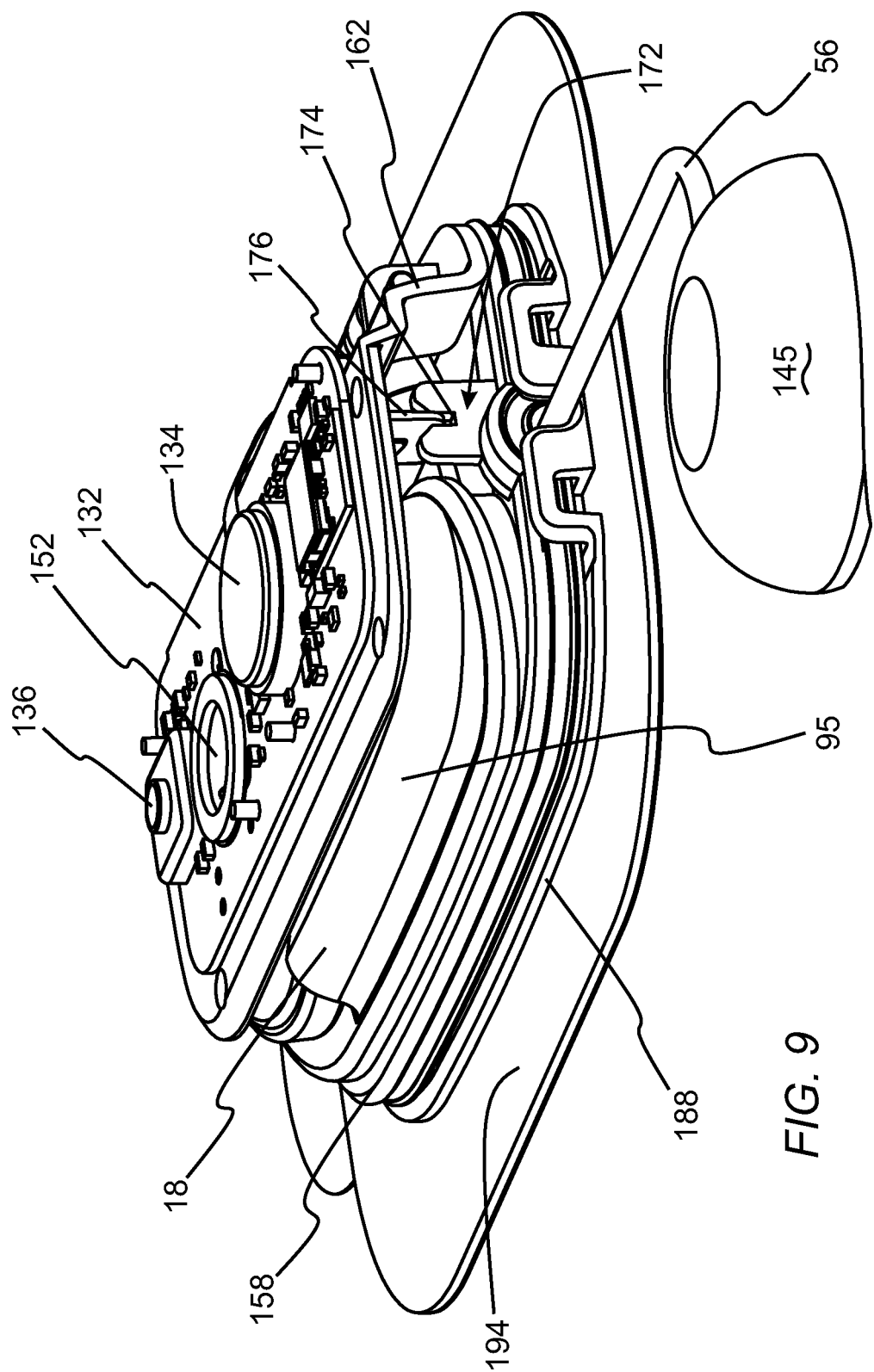
FIG. 9 is a perspective view of the medical pump system of FIG. 2 shown without the outer shell for purposes of illustration.

With regard to coupling the reservoir cartridge assembly 12 to the actuator assembly 14, in some instances, the actuator chassis 162 and the reservoir base 94 may include a mutual alignment feature 172 as shown in FIG. 9 which may be configured to be operatively and releasably coupled between the actuator chassis 162 and the reservoir base 94 that prevents relative lateral displacement between the actuator chassis 162 and the reservoir base 94. In some cases, the alignment feature 172 may include an alignment slot 174 secured in fixed relation to reservoir base 94 and an alignment rib 176 which is secured in fixed relation to the actuator chassis 162 with the alignment rib 176 being configured to fit tightly within the alignment slot 174. The arrangement could also be reversed with the alignment slot 174 disposed on the actuator chassis 162 and the alignment rib 176 disposed on the reservoir base 94. Any other suitable type of alignment feature 172 may be used as well in order to limit or prevent any relative lateral displacement between the actuator chassis 162 and reservoir base 94 during rotation of the cam assembly 68 against the pushrods of the pump assembly.

Figure 10:
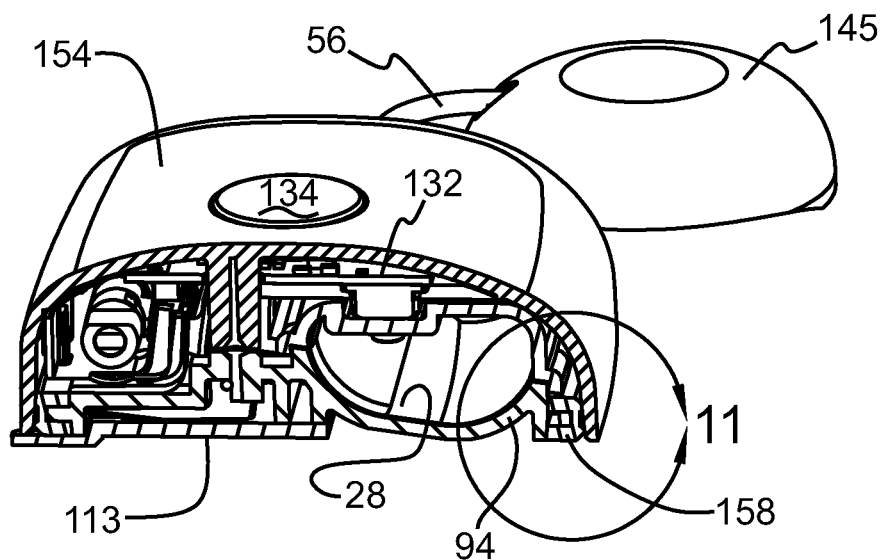
FIG. 10 is a perspective view in transverse section of the medical pump system embodiment of FIG. 2.
Figure 11:
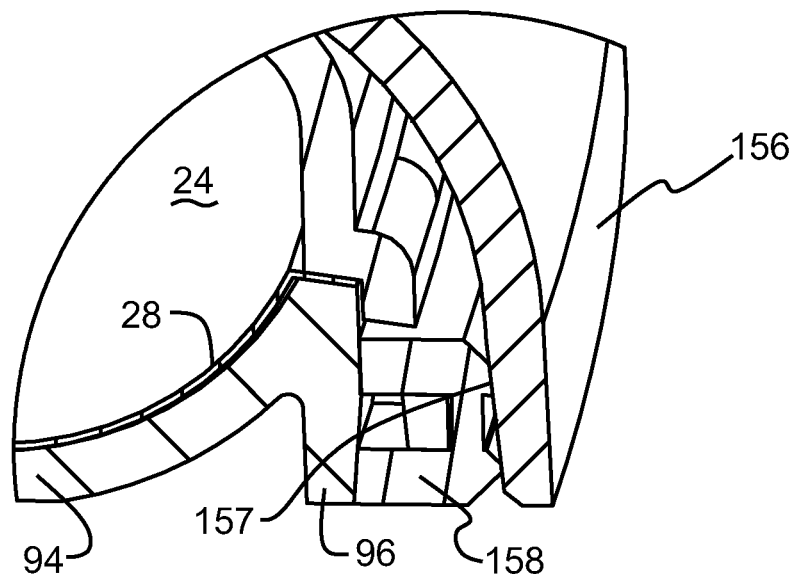
FIG. 11 is an enlarged view of the medical pump system embodiment of FIG. 10 indicated by the encircled portion 11-11 in FIG. 10.

For some embodiments, the actuator assembly 14 may also include the outer shell 156 which may be a smooth continuous layer of rigid material which is disposed over and protects all of the components of the actuator assembly 14 from environmental elements, including moisture. As such, in some cases, an outer shell seal 158 may be disposed about an outer perimeter 96 of the reservoir base 94, as shown in FIGS. 10 and 11, and be sized and configured to seal to an inside surface 157 of the outer shell 156 when the actuator assembly 14 is coupled to the reservoir cartridge assembly 12. In some cases, the outer shell seal 156 may include a flexible elastomer with a double lip transverse cross section as shown in FIGS. 10 and 11. The contact parameters between the inside surface 157 of the outer shell 156 and the outer shell seal 158 may be configured, in some instances, to provide a level IP24 rated seal therebetween.

Figure 18:
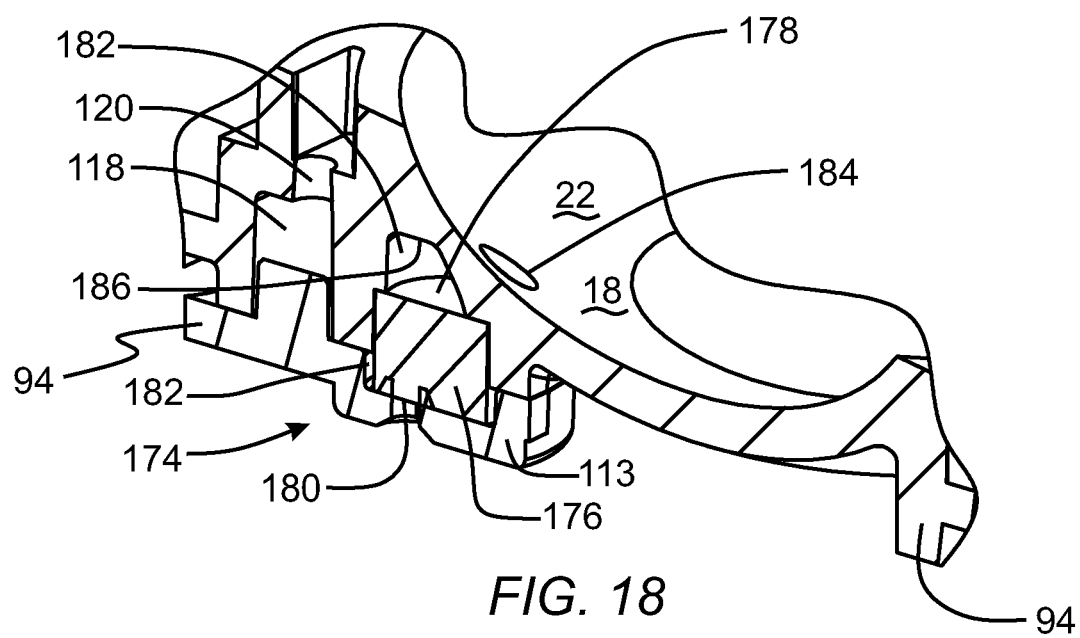
FIG. 18 is an enlarged perspective view, partially cut away of the reservoir cartridge assembly embodiment and showing a fill port embodiment thereof.

The reservoir cartridge assembly 12 may include a fill port 174 to facilitate manual filling of the liquid volume 22 of the fluid reservoir 18 as shown in FIG. 18 once the reservoir cartridge assembly 12 has been coupled to the actuator assembly 14. For some embodiments, the fill port 174 may include a fill septum 176 which has an inner surface 178, an outer surface 180 and which is disposed within a fill septum cavity 181. The fill septum cavity 181 may include an open portion 182 disposed adjacent the inner surface 178 of the fill septum 176. The open portion 182 may also be disposed in fluid communication with a fill passage 184. The fill passage 184 may in turn be disposed in fluid communication between the fill septum cavity 181 and the liquid volume 22 of the fluid reservoir 18. A patient may generally use the fill port 174 by filling an appropriately configured syringe with a desired therapeutic fluid 50 and inserting the hypodermic needle of the syringe (not shown) through the fill septum 176 and into the open portion 182 of the fill septum cavity 181 with a distal port of the hypodermic needle in fluid communication with the open portion 182 of the fill septum cavity 181. The syringe may then be emptied into the open portion 182 of the fill septum cavity 181 with the therapeutic fluid 50 so delivered flowing through the fill passage 184 into the liquid volume 22. In some instances, the open portion 182 may include a needle stop surface 186 formed by an inner surface of the fill septum cavity 181 disposed opposite the inner surface 178 of the fill septum 176. The needle stop surface 186 may be configured and positioned to prevent unwanted penetration of the hypodermic needle into fragile components of the medical pump system 10. For some embodiment, the fill septum 176 may include an elastic polymer such as polyurethane, silicone or the like.

Figure 2:
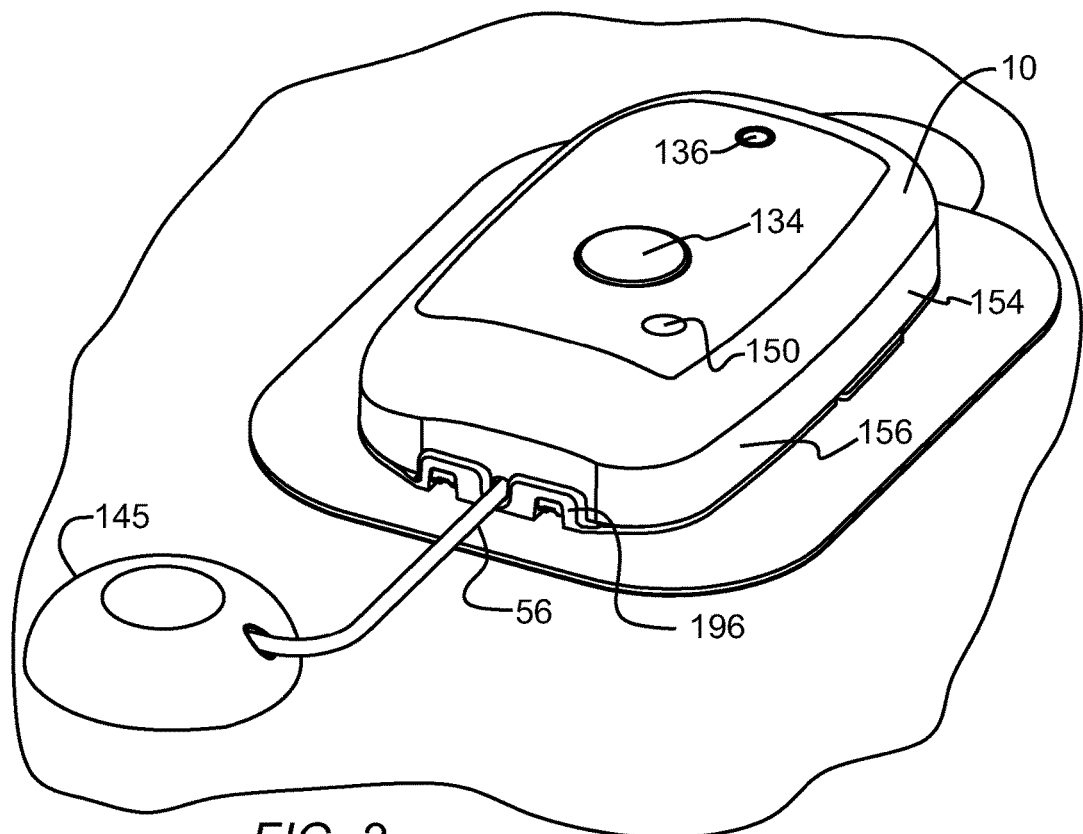
FIG. 2 is a perspective view of a medical pump system embodiment.

Once the liquid volume 22 of the fluid reservoir 18 of the medical pump system 10 has been filled, the patient will generally attach the medical pump system 10 to a desired position on their body. Some embodiments of the medical pump system 10 discussed above may include an optional mount bracket 188 that may be used to releasably secure the coupled actuator assembly 14 and reservoir cartridge assembly 12 to an outer surface of the patient's skin 143 in a desired location. Referring to FIGS. 2-4, the mount bracket 188 may include a bracket body 190 having an adhesive layer 192 disposed on a bottom surface of an adhesive pad 194 that is secured to the bracket body 190. Typically, the adhesive surface of the adhesive layer 192 will be covered by a peel off layer that maintains the integrity of the adhesive surface until ready for use. The bracket body 190 may have an outer contour that generally matches an outer contour of the perimeter of the outer shell 156 of the actuator assembly 14. The bracket body 190 also includes a plurality of mount receptacles 196 that are configured to receive corresponding mount tabs 198 disposed on the outer perimeter of the outer shell 156 (see also FIG. 7).

One of the mount receptacles 196 may include a flexible bail 200 that may have a resilient flexibility that allows a mating mount tab 198 of the outer shell 156 to be snapped into place with an opening of the flexible bail 200 mechanically capturing the mating mount tab 198. Once the end user patient is ready to remove the actuator assembly 14 from the mount bracket 188, the flexible bail 200 may be elastically flexed outwardly away from the outer shell 156 so as to disengage the flexible bail 200 from the mating mount tab 198 disposed therein thereby releasing the actuator assembly 14 and reservoir cartridge assembly 12 coupled thereto from the mount bracket 188. The flexible bail 200 is elastically deformed and thus reusable if desired. For some mount bracket embodiments 188, the adhesive pad 194 may have a length of about 2.5 inches to about 3 inches, a width of about 2 inches to about 2.5 inches and a thickness of about 0.2 inches to about 0.5 inches. The adhesive surface 192 may include any adhesive suitable for skin contact including acrylate type adhesives or the like.

The coupled actuator assembly 14 and reservoir cartridge assembly 12 may also be attached to the patient's body 142 in other ways. For example, in some cases, a flexible polymer layer 141 separate from the medical pump system 10 may be used. As such, for some kit embodiments that include medical pump system embodiments 10, such a kit may also include an optional flexible polymer layer or patch 141 shown schematically in FIG. 3 which is sized to fit over the actuator assembly 14 and assembled medical pump system 10 as a whole. The flexible polymer patch 141 may include an adhesive backed perimeter portion which is configured to be releasably secured to a patient's skin 143. For some embodiments, the flexible polymer patch 141 may have at least one vent hole disposed therethrough. For such an application, the flexible polymer patch 141 may be disposed over the medical pump system 10 against the patient's skin 143 and the adhesive backed perimeter portion thereof secured to the patient's skin 143 creating a pouch against the patient's skin 143 in which the medical pump system 10 may be disposed. Once the medical pump system 10 needs to be removed or otherwise accessed, the flexible patch would be removed from the patient's skin 143 and a new flexible patch 141 used to reattach the medical pump system 10 to the patient. Typically, the flexible polymer patch 141 would be made of a clear flexible material that would permit operation of the control button 134 and priming button 136 and would also transmit any audio or visual signals therethrough.

In some cases, a patient may initiate use of medical pump system embodiments 10 discussed herein by coupling the reservoir cartridge assembly 12 to the actuator assembly 14 to form the medical pump system 10. In some cases, the coupling of the reservoir cartridge assembly 12 to the actuator assembly 14 may be detected by the controller 88 by the controller 88 which detects electrical power being supplied to the controller 88. The controller 88 may then initiate a power-on-self-test once the controller 88 has detected electrical power being supplied to the controller 88. In addition, a time point zero may be stored into a memory 91 of the controller 88 and a power source voltage check initiated by the controller 88. In some instances, at this stage, the controller 88 may be configured to perform one complete rotation of the cam assembly 68 or cam shaft 70 of the actuator assembly 14 with the cam shaft 70 coming to a stop in an angular position wherein the inlet port 42 of the pump chamber assembly 32 of the reservoir cartridge assembly 12 is closed and the vent port 100 of the pump chamber assembly 32 of the reservoir cartridge assembly 12 is open to the ambient atmosphere.

Figure 19A:
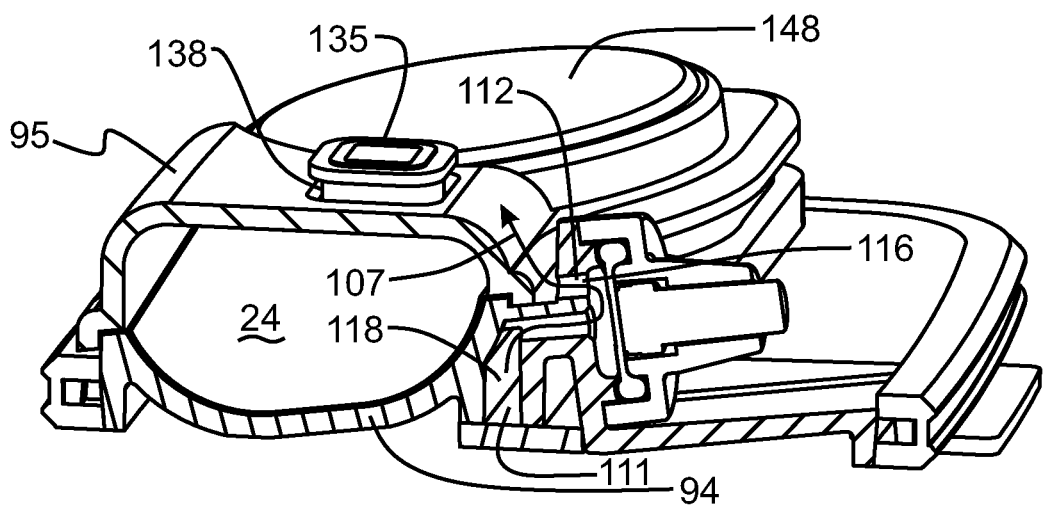
FIGS. 19A-19C are transverse cross section views of a reservoir cartridge subassembly and illustrating a fill sequence of the fluid volume of a fluid reservoir thereof.
Figure 19B:
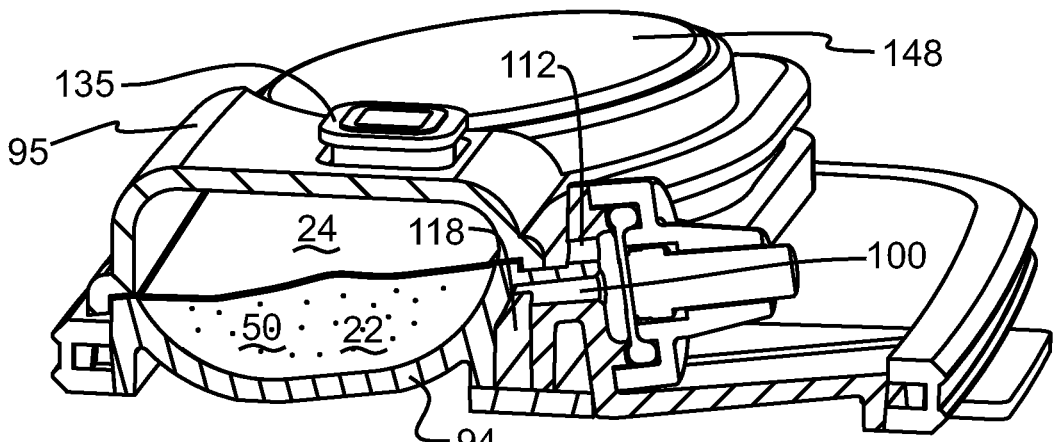
Figure 19C:
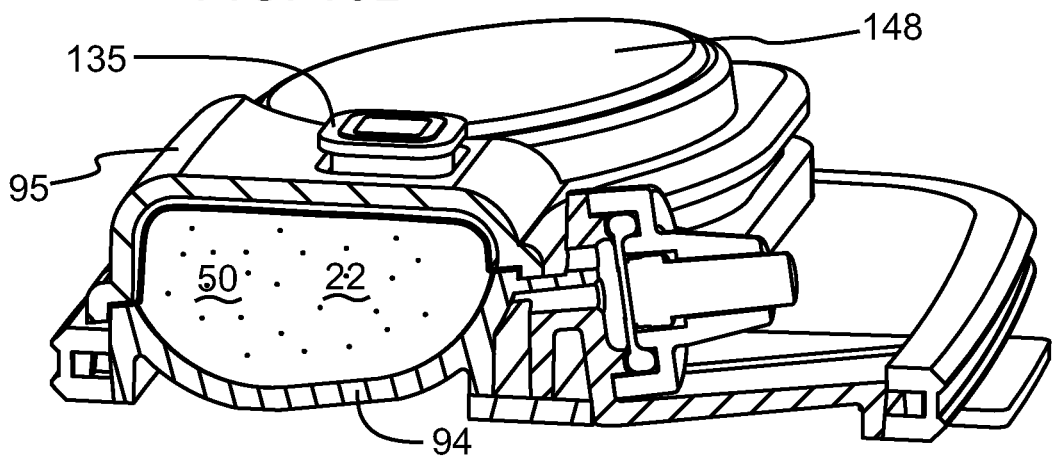

Thereafter, the liquid volume 22 of a fluid reservoir 18 of the reservoir cartridge assembly 12 may be manually filled with the therapeutic fluid 50 while venting air from the air volume 24 disposed adjacent the liquid volume 22. The liquid volume 22 may be filled through the fill port 174 with a syringe or other suitable source of desired therapeutic fluid 50. As discussed above, the therapeutic fluid 50 injected into the fill port 174 flows through the fill passage 184 and into the liquid volume 22 bounded by a fluid cavity molded into the reservoir base 94 and the flexible membrane 28 sealed thereto. In some cases, the flexible membrane 28 may be pre-molded or otherwise form fitted to the fluid cavity molded into the reservoir base 94 to reduce or eliminate any air pockets in the liquid volume 22 when the liquid volume is empty as shown in FIG. 19A. As therapeutic fluid 50 flows into the liquid volume space, the flexible membrane 28 begins to distend and separate from the fluid cavity surface of the reservoir base 94 as the incoming therapeutic fluid begins to displace the flexible membrane as illustrated by the partially filled liquid volume shown in FIG. 19B. The liquid volume 22 may continue to be filled through the fill port 174 until the liquid volume 22 of the fluid reservoir 18 is completely filled with the flexible membrane 28 being pressed up against or adjacent to the fluid reservoir cover 95 as shown in FIG. 19C. For some embodiments, the fluid reservoir cover 95 as well as the reservoir base 94 may be formed from clear polymer materials in order for a patient to be able to visualize the fill level within the liquid volume 22 of the fluid reservoir 18.

The outlet conduit 56 of the pump chamber assembly 32 may be primed by activating the priming button 136 of the actuator assembly 14 and the medical pump system 10 releasably secured to the patient. In some instances, releasably securing the medical pump system 10 to the patient may include removing a backing of the adhesive pad 194 of the mount bracket 188 of the medical pump system embodiment 10, applying the adhesive surface 192 of the adhesive pad 194 to the patient's skin 143 in a suitable location and releasably securing the actuator assembly 14 and reservoir cartridge assembly 12 of the medical pump system 10 to the mount bracket 188. In other cases, releasably securing the medical pump system 10 to the patient may include disposing a flexible polymer layer over the medical pump system 10 and sealing the perimeter of the flexible polymer layer to the patient's skin 143 around the medical pump system 10 as discussed above. Once the medical pump system 10 is so secured, the outlet conduit 56 of the pump chamber assembly 32 may be disposed in fluid communication with a subcutaneous delivery site 140 within the patient's body 142. A controlled rate of infusion, such as a basal rate, of the therapeutic fluid 50 may then be delivered to the subcutaneous delivery site 140 of the patient by performing sequential pumping cycles of the medical pump system 10 carried out according to a predetermined delivery protocol.

In some instances, performing such a pumping cycle may include performing a fill cycle of the cam assembly 68 followed by performing a dispense cycle of the cam assembly 68 by rotation of the cam shaft 70. In some embodiments, performing a fill cycle by rotation of the cam shaft 70 may include disposing the inlet cam lobe 72 in a retracted position with an inlet port 42 of the pump chamber assembly 32 in an open position as shown in FIG. 14A. The fill cycle may also include disposing the outlet cam lobe 76 in an extended position with an outlet port 52 of the pump chamber assembly 32 in a closed position and disposing the displacement cam lobe 80 in an extended position. Thereafter, with the inlet port 42 open and the outlet port 52 closed, the displacement cam lobe 80 may be retracted as indicated by the arrow 202 in FIG. 14A so as to expand the displacement chamber 62 and draw therapeutic fluid 50 through the inlet port 42 and into the expanding displacement chamber 62 as indicated by arrow 204 in FIG. 14A until the displacement cam lobe 80 is fully retracted and the displacement chamber 62 is full of therapeutic fluid 50 as shown in FIG. 14B. During this fill cycle, the controller 88 may be configured to determine a fill level of the liquid volume 22 of the fluid reservoir 18 by monitoring a pressure drop within the air volume 24 of the fluid reservoir 18 with the controller 88 during the fill cycle. In addition, embodiments of the fill cycle may terminate by extending the inlet cam lobe 72 until the inlet port 42 is closed while maintaining the displacement cam lobe 80 in a retracted position and with the outlet port 52 closed as shown in FIG. 14B.

In some cases, performing the dispense cycle by rotation of the cam shaft 70 may include retracting the outlet cam lobe 76 and opening the outlet port 52 while the displacement chamber 62 is full of therapeutic fluid 50 and while the inlet port 42 is closed. The dispense cycle may also include extending the displacement cam lobe 80 as indicated by arrow 205 in FIG. 14B and reducing a volume of the displacement chamber 62 and dispensing the therapeutic fluid 50 disposed therein out of the outlet port 52 as shown by arrow 206 while the inlet port 42 is closed and the outlet port 52 is open. The dispense cycle may also include opening the vent port 100 of the pump chamber assembly 32 and venting the air volume 24 of the fluid reservoir 18 to an ambient atmosphere as indicated by arrow 107 during the dispense cycle. The dispense cycle, in some instances, may also include maintaining the vent port 100 in an open state and venting the air volume 24 of the fluid reservoir 18 to the ambient atmosphere while waiting for a subsequent dispense cycle so as to monitor ambient pressure and detect any unexpected ambient pressure profiles. During both the fill cycle and dispense cycle, rotation of the cam shaft 70 may be monitored by the controller 88 using the position sensor 144.

For some embodiments and delivery of certain therapeutic fluids 50, delivering a controlled rate of infusion, such as a basal rate, of the therapeutic fluid 50 may include delivering about 5 microliters to about 15 microliters of therapeutic fluid 50 per hour to the subcutaneous delivery site 140. For some embodiments, the fluid reservoir 18 may have a volume capacity of about 2 ml to about 5 ml, more specifically, about 2.8 ml to about 3.2 ml. Once the therapeutic fluid 18 disposed within the liquid volume 22 of the fluid reservoir 18 is used up, or close to being used up, an alarm signal may be triggered by the controller 88. In addition, with regard to a time limit for the reservoir cartridge assembly 12 programmed into the controller memory 91, expiry of the reservoir cartridge assembly 12 may indicated and triggered after about 60 hours of use to about 100 hours of use by activating an alarm signal with the controller 88. Such an alarm signal will be observable by the patient either visually or audibly.

Figure 20:
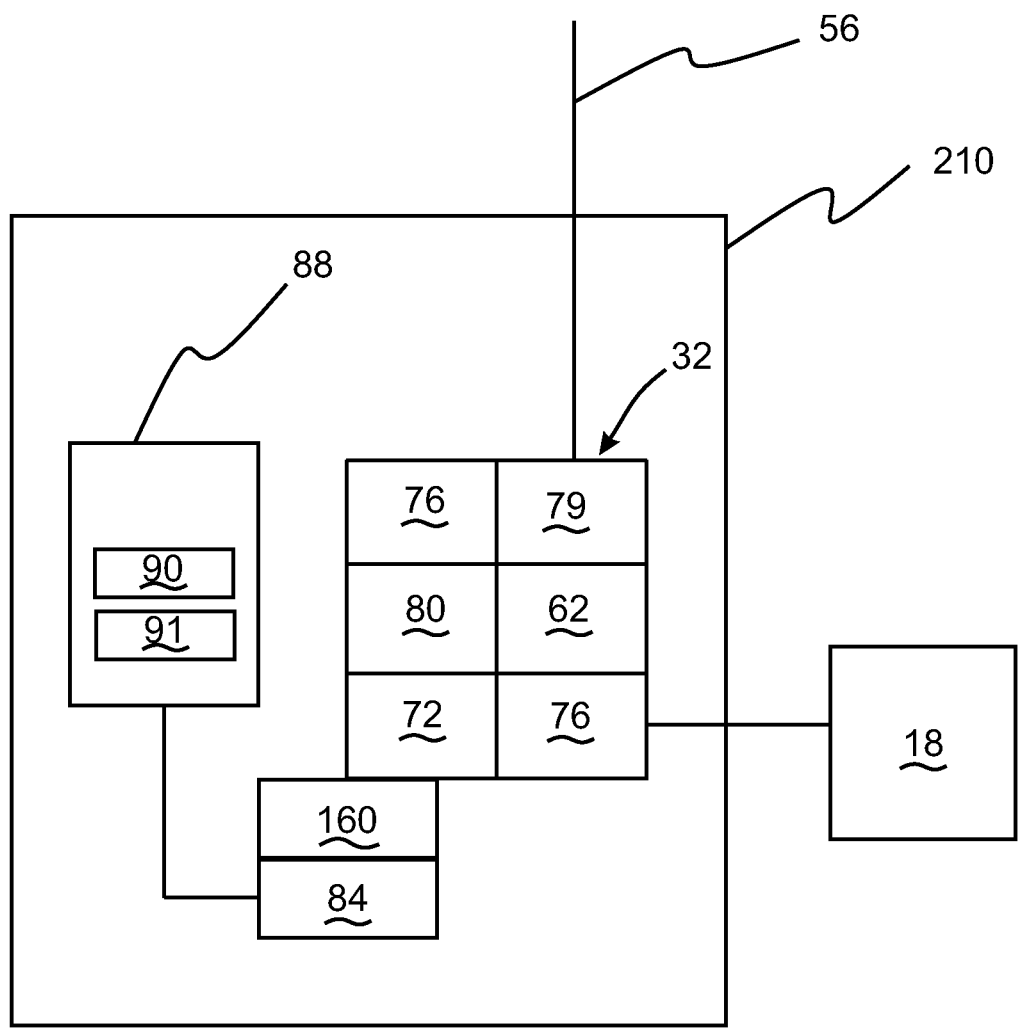
FIG. 20 is a schematic representation of a pump assembly embodiment.

In some cases, certain components or subassemblies of the medical pump system embodiments 10 discussed herein may be useful separately or as part of another pump system embodiment. Referring to FIG. 20, a schematic representation of a pump assembly embodiment 210 for medical use is shown that includes components of the medical pump system embodiments 10 discussed above and that may perform the same functions in the same manner as discussed above. The pump assembly embodiment 210 may include the pump chamber assembly 32 including the pump chamber 34 having an interior volume 36 which is at least partially bounded by the pump housing 38. The pump chamber assembly 32 may also include the inlet port 42 which is in fluid communication with the interior volume 36. The pump chamber assembly 32 may also include the resilient inlet membrane 44 which is disposed adjacent the inlet port 42, which is spaced from the inlet port 42 when in a relaxed state, and which is sufficiently distendable towards the inlet port 42 to seal the inlet port 42 when in a compressed state. The pump chamber assembly 32 may also include the outlet port 52 in fluid communication with the interior volume 36 and the resilient outlet membrane 54 which is disposed adjacent the outlet port 52, which is spaced from the outlet port 52 when in a relaxed state, and which is sufficiently distendable towards the outlet port 52 to seal the outlet port 52 in a compressed state. The displacement chamber 62 may also be disposed within the interior volume 36 and the resilient displacement membrane 64 is disposed adjacent the displacement chamber 62, which forms at least a portion of a boundary of the displacement chamber 62, which is sufficiently inwardly distendable from a relaxed state to reduce the volume of the displacement chamber 62 when in a compressed state. The resilient displacement membrane 64 may also be sufficiently resilient to increase the volume of the displacement chamber 62 when released from the compressed state.

The pump assembly 210 may also include an actuator assembly embodiment 14 having the cam assembly 68 with the cam shaft 70 that includes the inlet cam lobe 72 which is operatively coupled to the resilient inlet membrane 44, the outlet cam lobe 76 which is operatively coupled to the resilient outlet membrane 54, and the displacement cam lobe 80 which is operatively coupled to the resilient displacement membrane 64. The actuator assembly 14 may also include the motor 84 operatively coupled to the cam assembly 68 and the controller 88 operatively coupled to the motor 84. The power source 148 such as a battery may also be operatively coupled to the controller 88. All of the components of the pump assembly embodiment 210 shown in FIG. 20 may function in the same manner as discussed herein with regard to other pump system embodiments 10. In addition, for some embodiments, the inlet cam lobe 72 may be operatively coupled to the inlet valve assembly 75, the outlet cam lobe 76 may be operatively coupled to the outlet valve assembly 79 as well as the displacement cam lobe 80 being operatively coupled to the displacement chamber and its associated components including the displacement pushrod 82.

Proper compliance with regard to use of medical devices may typically be achieved by providing instructions for use (IFU) to a patient or treating physician. Such IFUs often include an overwhelming amount of information and warnings forewarning against negative consequences. Due to the patient's challenge in becoming acceptably knowledgeable, educators and physicians are often required to provide a personal level of education and training support for treatments being administered. This practice may, in some circumstances, create a financial burden to the patient end user and also result in inconsistent success rates with regard to compliance due to the lack of consistency in training methods.

Devices that require user input in order to complete a specific function related to the therapy being administered may have reduced effectiveness if used the patient end user does not fully understand how to complete the specific function correctly. For instance, use of an ambulatory insulin infusion pump intended for use by an end user patient with diabetes that does not have any professional medical training typically requires the end user to select a quantity of insulin to be infused based on the current blood sugar level or meal they plan to consume which may be fairly complicated in some instances. As such, it may be desirable to provide a device and/or method for such an end user to engage in hands on training of the particular device they will be using without the risk of a potentially costly mistake in order to gain familiarity and confidence prior to actual therapeutic use.

Figure 21:
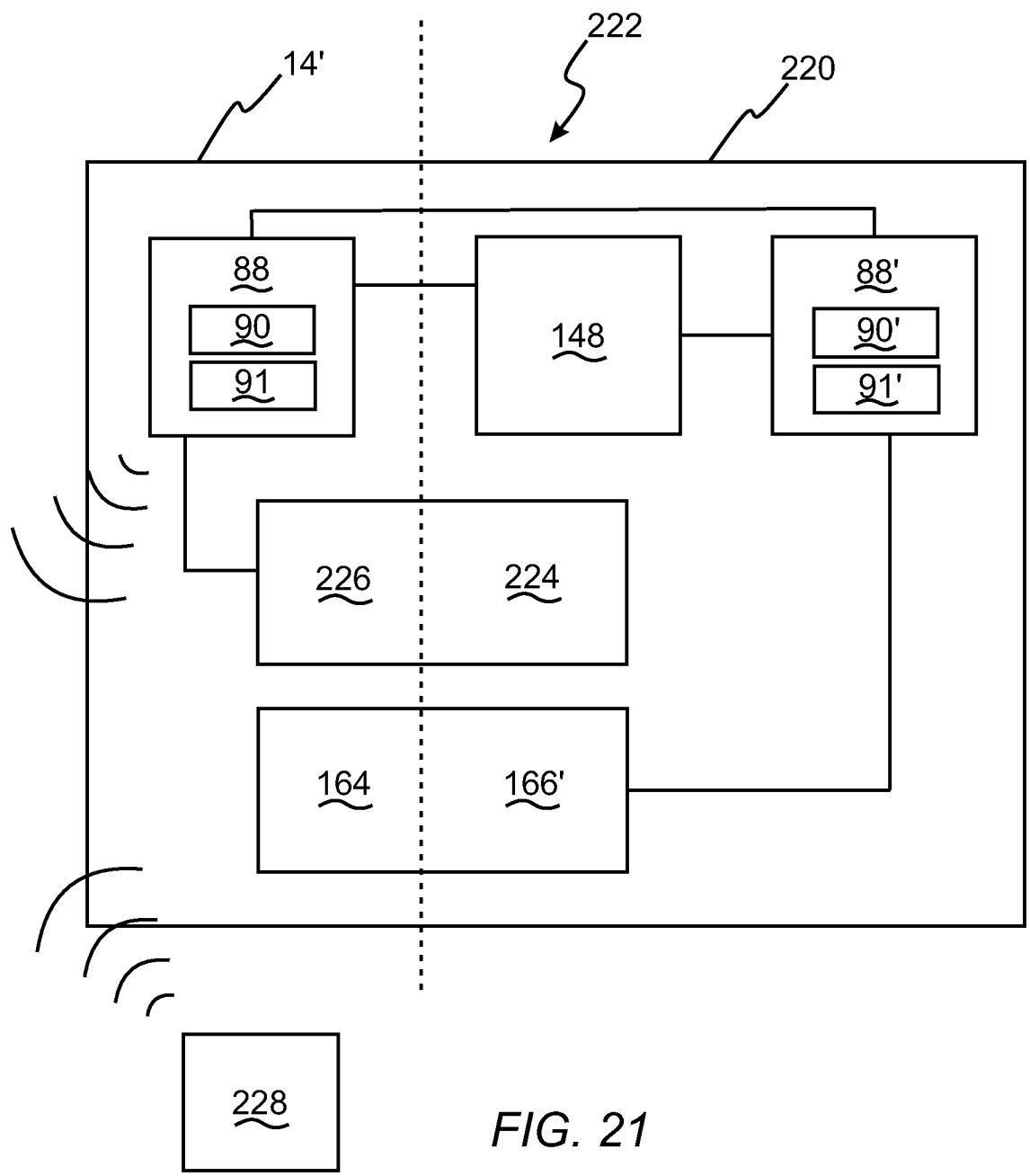
FIG. 21 is a schematic representation of a medical pump training system embodiment.

As such, certain medical devices, such as medical pump systems 10 or components thereof may be supplied with an attachable training module or cartridge 220 that may be combined to form a medical pump training system 222 as schematically illustrated in FIG. 21. Such a medical pump training system 222 may enable the end user patient to simulate the use of the medical device in a safe environment without the risk of wasted medical materials or equipment. The schematic overview of the embodiment of the medical pump training system 222 shown in FIG. 1 includes a dashed line which indicates a coupling interface between the actuator assembly 14' and the training cartridge 220 of the medical pump training system 222, and the various components thereof. The coupling interface represents the physical point of separation between the respective components of each of the actuator assembly embodiment 14' and training cartridge 220 that interface with each other when the actuator assembly 14' and training cartridge 220 are coupled together. The interconnecting lines between the various schematic components of FIG. 21 may include any type of suitable conduit that may be useful for operatively interconnecting the components such as information conducting conduits, power conducting conduits or the like including conductive wires, optical fibers, wireless connectivity etc. In general, the actuator assembly embodiment 14' may include any or all of the components of the actuator assembly 14 discussed above. The actuator assembly embodiment 14' in FIG. 21 is shown without any of the cam lobes 72, 76, 80 or 104 for clarity of illustration and because these components of the actuator assembly may not typically have any counterpart components in the training cartridge 220 to interface with. Likewise, the motor 84 and transmission 160 of the actuator assembly embodiment 14' are not shown for purposes of clarity of illustration.

In the case of medical pump embodiments, such as insulin pump embodiments, such a training cartridge 220 may be installed in place of the reservoir cartridge assembly 12 (reservoir) that includes or could include therapeutic materials, thereby eliminating the potential risk of over infusion of a drug, such as insulin, and allow the end user to be accustomed to the associated device inputs, outputs, interface protocols etc. For some embodiments, such a training cartridge 220 may also allow the therapeutic device, such as the actuator assembly embodiments 14' to receive updates to software stored in the memory 91, 91' of the respective controllers 88, 88', or customizations in firmware, ensuring the device 14' is in a safe mode that minimizes the risk to the user. This type of arrangement may be particularly useful for medical pump system embodiments 10 that include a durable element and a low use or disposable element, such as the actuator assembly embodiments 14 and reservoir cartridge assembly embodiments 12 discussed above.

With regard to medical pump systems 10 as discussed herein, as well as others, suitable training cartridge embodiments 220 may include certain elements that are typically included in a therapeutic cartridge in order to enable functioning of the system as a whole. In particular, some embodiments of the training cartridge 220 for use with the actuator assembly embodiments 14' discussed herein may be used in place of the reservoir cartridge assembly embodiments 12 discussed herein. The training cartridge 220 may include an element that provides power to a functioning actuator assembly 14' and may be configured to latch onto the actuator assembly 14' in a similar fashion to that of the reservoir cartridge assemblies 12 (disposable) enabling the end user to exercise the physical elements of the medical pump system embodiments 10 and become familiar/comfortable with them.

In some cases, it may be desirable for the latch spring 166' of the training cartridge 220, as shown in FIG. 21, to be reusable so that the training cartridge 220 may be used multiple times for multiple training sessions. As such, the training cartridge 220 may be configured to be reused and reattached while the therapeutic reservoir cartridge assembly embodiments 12 discussed herein are generally intended for single use and have a single use release latch 166. As such, the latch spring 166' may be configured to not include the disabling feature 167 that is part of the latch mechanism 16 discussed above or may include any other suitable features or lack thereof that configures the latch mechanism of the training cartridge 220 to be reusable. In addition, for some embodiments of the training cartridge 220, the portion of the latch mechanism housed in the training cartridge 220, may include an electro-mechanical structure that is configured to be releasably secured to the latch post 164, and controllable by the controller 88' in order to be released from the latch post 164.

The training cartridge embodiments 220 may also have a means for the mating actuator assembly 14' to differentiate the training cartridge 220 from the therapeutic reservoir cartridge assembly embodiments 12 so the actuator assembly 14' configures itself to operate in a training mode. In some cases, when the actuator assembly 14' is coupled to the training cartridge 220, the controller 88 may be disposed in operative communication with the controller 88', and the controller 88' may be configured to identify the training cartridge 220 by communicating an identification signal to the controller 88. In addition, other techniques for establishing such differentiation may include providing a certain identifying feature or features 224 on the training cartridge 220 that may be read or otherwise interpreted by an optional reader 226 that may be operatively coupled to the controller 88. In some cases, the training cartridge 220 may also include an optional training module controller 88' that may be operatively coupled to power source 148 as well as the controller 88 of the actuator assembly 14'. Such a training cartridge controller 88' may be configured to communicate with the controller 88 of the actuator assembly 14' and provide identifying information, training programs and the like.

Regarding examples of identifying features 224, some embodiments of the training cartridge 220 may include an identifying feature 224 including NFC tag, a 2D barcode on training cartridge with read camera 226 on actuator assembly 14', a resistive label disposed on the training cartridge 220 with corresponding contacts on actuator assembly 14', a mechanical feature disposed on the training cartridge 220 that actuates a switch 226 on the actuator assembly 14' or a magnet on the training cartridge and hall effect sensor 226 on actuator assembly 14'.

In use, for some embodiments, a training mode may provide specific user functions and disengage critical alarms caused from failure detections on the actuator assembly 14' (e.g., occlusion detection, low insulin, pump malfunction). The actuator assembly 14' may, in some cases, wirelessly connect (BLE) to a remote mobile device 228, such as a smart phone or the like with supporting application as shown in FIG. 21. In some cases, a training mode of the actuator assembly 14' may unlock a training section of the phone application. For some embodiments, the remote mobile device 228 may be configured to provide real time guidance and feedback to a user of the device based on a status of a condition being monitored by the controller 88, or in some cases, controller 88'. In some instances, the remote mobile device 228 may be configured to communicate status data regarding conditions being monitored by the controller 88, or in some cases controller 88', to a cloud data management system through a wireless connection between the remote mobile device 228 and the cloud data management system (not shown). Such a training application for a remote mobile device 228 or the like may include providing tutorials, videos, and/or a dashboard providing additional information on actuator assembly features. The training mode of the actuator assembly 14' may also include the ability to switch from training mode to operation mode based on pump feedback driven by the training cartridge 220 being installed. A connection to a data portal or the like in order to upload status and provide real time tracking and support of the actuator assembly 14' or any other component of the medical pump system 10 from an administrative account. In some cases, support analysis of user training sessions may be communicated to the controller 88 in order to ensure that the medical pump system 10 or components thereof are being utilized in a safe and useful manner.

Figure 22:
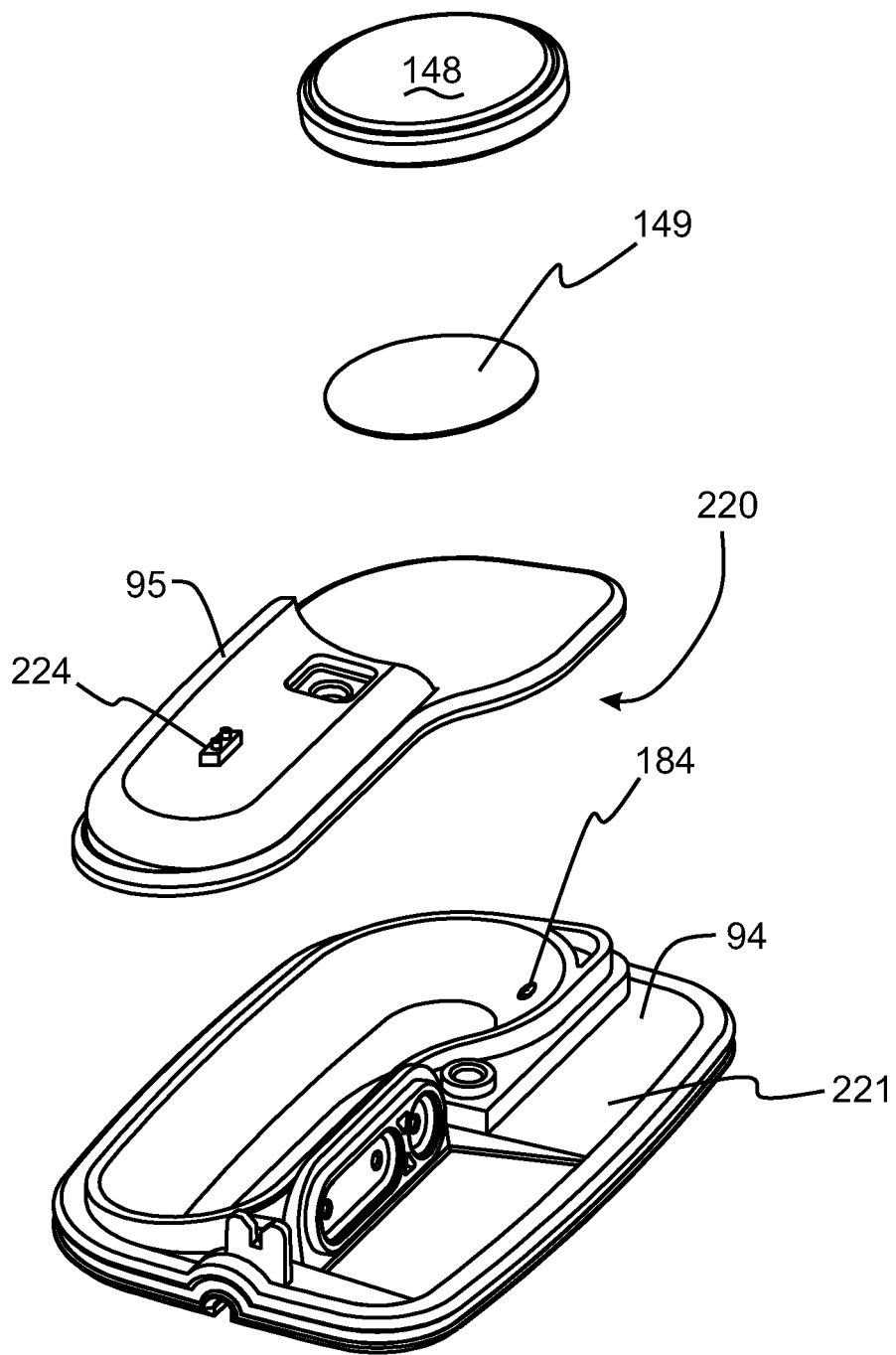
FIG. 22 is an exploded view of a training cartridge embodiment.
Figure 23:
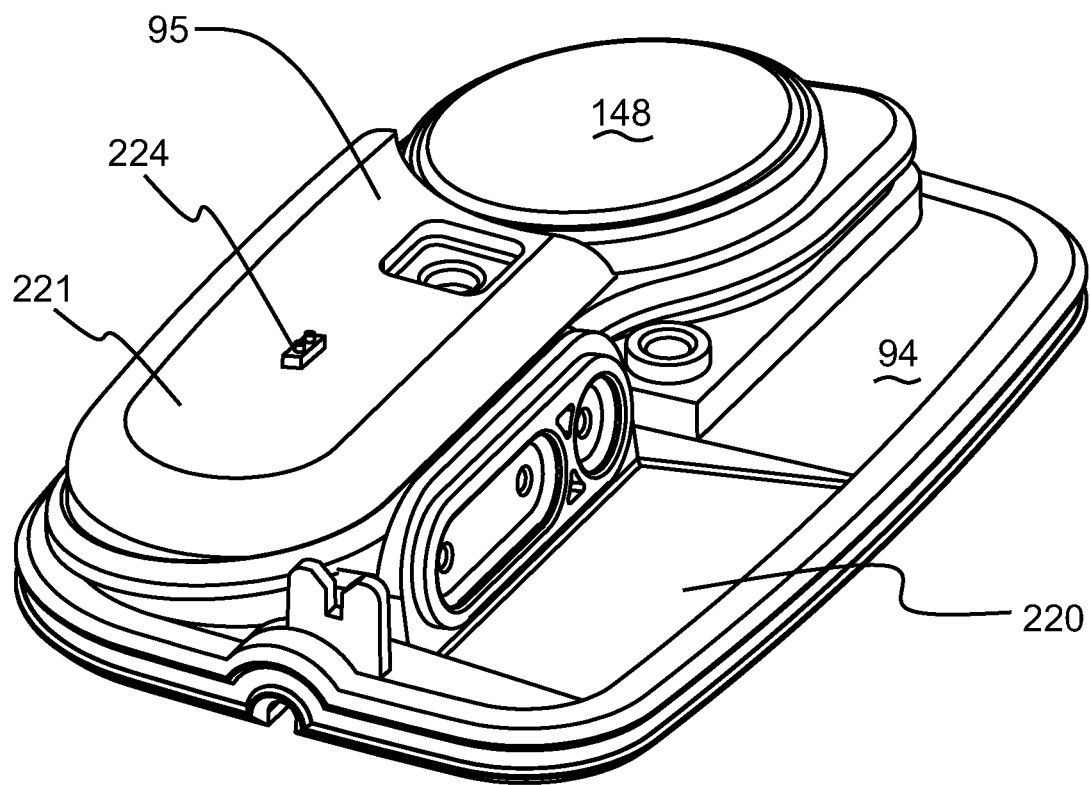
FIG. 23 is a perspective view of the training cartridge embodiment of FIG. 22.

Referring to FIGS. 21-23, a medical pump training system 222 is shown that may include the actuator assembly 14' having an actuator chassis 162 and the controller 88 secured to the actuator chassis 162. The medical pump training system 222 may also include the training cartridge 220 having a cartridge housing 221 which is configured to releasably couple to the actuator assembly 14' and which includes the identifying feature 224 that is configured to be operatively coupled to the controller 88 of the actuator assembly 14' and provide information to the controller 88 identifying the training cartridge 220 as a non-therapeutic cartridge. In some cases, the identifying feature 224 may be operatively coupled to the controller 88 by means of the reader 226 which may be operatively coupled to both the controller 88 and the identifying feature 224.

In some cases, a memory 91 of the controller 88 may include instructions, which may include machine readable instructions, to initiate a training program for a patient once the controller 88 identifies the training cartridge 220 by receiving the information from the identifying feature 224.

As discussed above, suitable examples of identifying feature embodiments 224 may include an NFC tag. The identifying feature 224 may also include a 2D barcode disposed on the training cartridge 220 and the actuator assembly 14' may further include a read camera 226 which is configured to read the 2D barcode. In some instances, the identifying feature 224 may be a resistive label and in such cases the actuator assembly 14' may have corresponding electrical contacts that are configured to operatively couple to the resistive label such that the controller 88 will be configured to determine the resistance of the resistive label and identify the training cartridge 220. For some embodiments, the identifying feature 224 may include a mechanical feature and the actuator assembly 14 further comprises a switch and the mechanical feature is configured to actuate the switch on the actuator assembly 14'. In some cases, the identifying feature 224 may include a magnet disposed on the training cartridge 220 and the actuator assembly 14' may have a corresponding a hall effect sensor which is configured to be operatively coupled to the magnet to enable the controller 88 which is operatively coupled to the hall effect sensor to identify the training cartridge 220. As noted above, it may be desirable for the training cartridge 220 to be reusable. As such, in some instances, the cartridge housing 221 may further include a reusable latch spring 166' that is configured to releasably couple to a latch post 164 which is secured in fixed relation to the actuator assembly 14'.

Some embodiments of a training cartridge 220 for a medical pump system 10 may include the cartridge housing 221 that is configured to couple to an actuator assembly 14' of the medical pump system 10 and the identifying feature 224 disposed on the cartridge housing 221 that is configured to be operatively coupled to a controller 88 of the actuator assembly 14' and provide information to the controller 88 identifying the training cartridge 220. For some such training cartridge embodiments 220, the cartridge housing 221 may further include the reusable latch spring 166' that is configured to releasably couple to the latch post 164 of the actuator assembly 14'.

Figure 24:
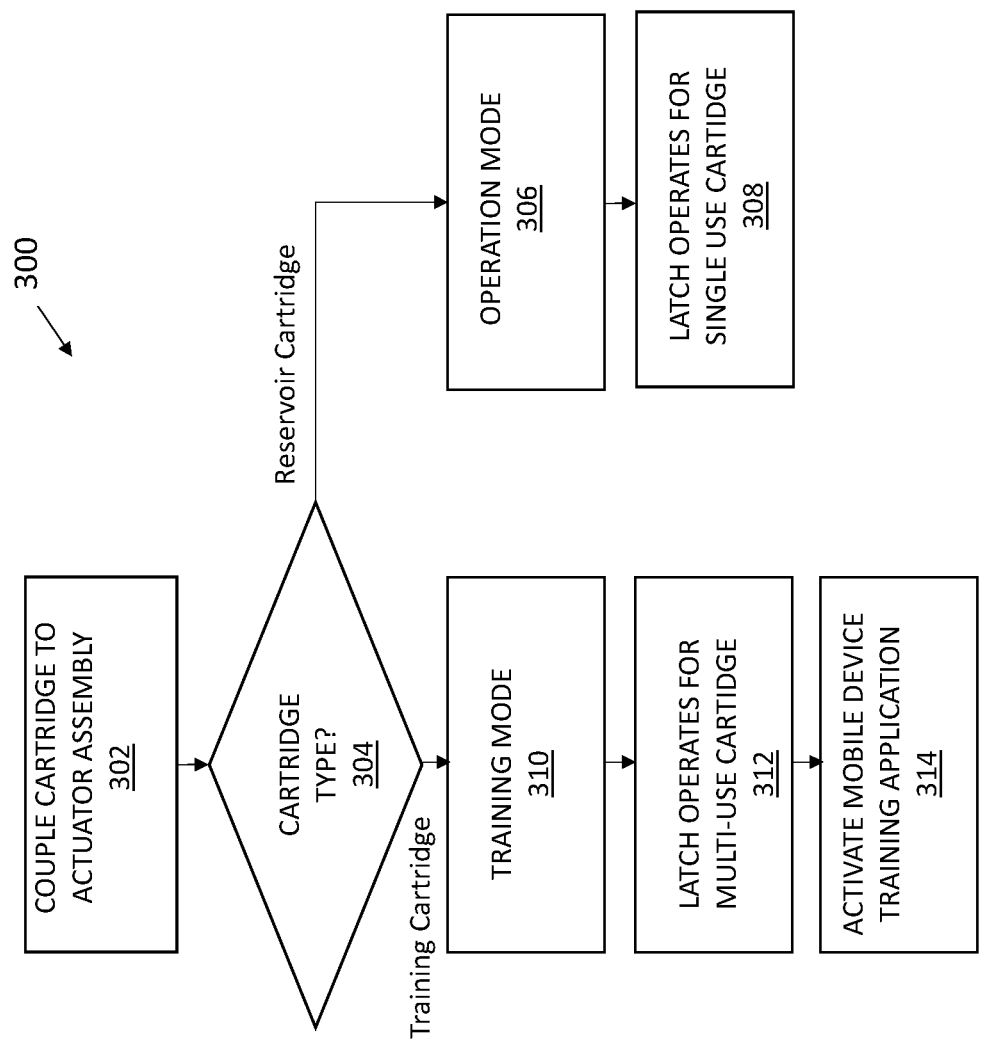
FIG. 24 is a flowchart indicating a method of communication between components of a medical pump training system embodiment.

Referring to FIG. 24, a method 300 for operating embodiments of the medical pump system 10 is shown. When describing the method 300, reference is made to elements of the actuator assembly 14' described herein. At step 302, a cartridge is coupled to the actuator assembly 14, for example. In some cases, the cartridge being so coupled may be either a reservoir cartridge assembly embodiment 12 or a training cartridge 220. In doing so, power (voltage, current, etc.), data and control signals, and/or therapeutic fluid 50 or other matter are capable of exchange between the actuator assembly 14' and the cartridge. At decision diamond 304, a type of cartridge is determined. In some embodiments, the type of cartridge is determined by hardware, for example, one or more interfaces, input/output devices, or the like of the actuator assembly 14'. In other embodiments, the type of cartridge is determined by software, for example, stored in a computer memory at the cartridge, the actuator assembly 14', or an external computer location, such as a remote computer, a cloud computing environment, and so on that communicates with the actuator assembly 14' and/or cartridge to identify the type of cartridge. In other embodiments, the cartridge is identified by a combination of hardware and software.

If at decision diamond 304, a reservoir cartridge assembly 12 is identified as coupled to the actuator assembly 14', then the method 300 proceeds to step 306 where the medical pump system 10 is in an operation mode, for example, capable of use for delivery of a therapeutic fluid 50 to a patient end user. At step 308, the latch mechanism 16 as part of a coupling mechanism between the reservoir cartridge assembly 12 and the actuator assembly 14', for example, the latch spring 166 shown in FIGS. 1 and 8, operates to permit a single use of the reservoir cartridge assembly 12 and prohibits a subsequent coupling of the same reservoir cartridge assembly 12 to the actuator assembly 14'. If at decision diamond 304, a training cartridge 220 is identified as coupled to the actuator assembly 14', then the method 300 proceeds to step 310, where the medical pump is in a training mode, for example, capable of training a user. At step 312, the latch 16 as part of a coupling mechanism between the training cartridge 220 and the actuator assembly 14, for example, the latch spring 166' shown in FIG. 21, operates to permit multiple uses of the training cartridge 220.

At step 214, the medical pump system 10 can connect wirelessly, for example, using BLE or other wireless interface, to a remote mobile device, such as a smartphone 228 or other computer having display or other input/output devices for permitting a trainee or other user to communicate with the medical pump system 10. When the training mode is determined at step 310, at step 314 the remote mobile device 228 may include an application that is activated, or unlocked, for example, in response to a receipt of a signal comprising data from the controller 88' of the training module 220. Returning to decision diamond 304, although a decision is made here whether the medical pump system 10 is in an operation mode or a training mode, some embodiments may include the ability to switch from the training mode to the operation mode based on pump feedback or other data driven by the training module 220.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A medical pump training system, comprising:
an actuator assembly including an actuator chassis and a controller secured to the actuator chassis; and
a training cartridge including a cartridge housing which is configured to releasably couple to the actuator assembly and which includes an identifying feature that is configured to be operatively coupled to the controller of the actuator assembly and to provide information to the controller identifying the training cartridge as a non-therapeutic cartridge, wherein the training cartridge is devoid of therapeutic materials, and wherein the training cartridge is installed with the actuator assembly in place of a reservoir assembly cartridge that includes the therapeutic materials to exchange software with the actuator assembly in the absence of the therapeutic materials, the training cartridge including a power source that provides power to the controller of the actuator assembly via a power conducting conduit extending between the actuator assembly and the training cartridge, wherein the actuator assembly is configured to exchange data with a remote mobile device, and wherein the actuator assembly includes a training mode that unlocks a training section of an application of the remote mobile device.

2. The medical pump training system of claim 1 wherein a memory of the controller includes instructions to initiate a training program for a patient once the controller identifies the training cartridge by receiving the information from the identifying feature.

3. The medical pump training system of claim 1 wherein the identifying feature comprises an NFC tag.

4. The medical pump training system of claim 1 wherein the identifying feature comprises a 2D barcode disposed on the training cartridge and wherein the actuator assembly further comprises a read camera which is configured to read the 2D barcode.

5. The medical pump training system of claim 1 wherein the identifying feature comprises a resistive label and the actuator assembly further comprises electrical contacts that are configured to operatively couple to the resistive label.

6. The medical pump training system of claim 1 wherein the actuator assembly further comprises a switch and the identifying feature is configured to actuate the switch on the actuator assembly.

7. The medical pump training system of claim 1 wherein the identifying-feature comprises a magnet disposed on the training cartridge and the actuator assembly further comprises a hall effect sensor which is configured to be operatively coupled to the magnet.

8. The medical pump training system of claim 1 wherein the cartridge housing further comprises a reusable spring latch that is configured to releasably couple to a latch post which is secured in fixed relation to the actuator assembly.

9. The medical pump training system of claim 1 further comprising a remote mobile device in wireless communication with the controller.

10. The medical pump training system of claim 9 wherein the remote mobile device is configured to provide real time guidance and feedback to a user based on a status of a condition being monitored by the controller.

11. The medical pump training system of claim 9 wherein the remote mobile device is configured to communicate status data regarding conditions being monitored by the controller to a cloud data management system through a wireless connection to the cloud data management system.

12. The medical pump training system of claim 1, wherein the actuator assembly includes a pumping mechanism, and wherein the training cartridge comprises a controller that communicates with the controller of the actuator assembly to control the pumping mechanism.

13. The medical pump training system of claim 1, wherein the training cartridge generates pump feedback, and wherein the training mode of the actuator assembly transitions from the training mode to an operation mode in response to the pump feedback provided by the training cartridge.

* * * * *